United States Patent [19]
Ono et al.

[11] Patent Number: 5,959,215
[45] Date of Patent: Sep. 28, 1999

[54] HEAT BUILD-UP/FATIGUE MEASURING METHOD FOR VISCOELASTIC BODY AND HYDRAULIC SERVO FLEXOMETER

[75] Inventors: Shigeki Ono, Tokyo; Chikahiro Satoh; Akira Yamada, both of Kunitachi, all of Japan

[73] Assignee: Bridgestone Corporation, Tokyo, Japan

[21] Appl. No.: 08/750,053

[22] PCT Filed: Sep. 5, 1995

[86] PCT No.: PCT/JP95/01762

§ 371 Date: Dec. 4, 1996

§ 102(e) Date: Dec. 4, 1996

[87] PCT Pub. No.: WO95/31887

PCT Pub. Date: Nov. 30, 1995

[30] Foreign Application Priority Data

Apr. 12, 1995 [JP] Japan ................................ 7-087163

[51] Int. Cl.⁶ .................................................. G01N 19/08
[52] U.S. Cl. ................................................ 73/798; 73/789
[58] Field of Search ............................ 73/789, 790, 794, 73/798, 799, 808, 810, 811, 866

[56] References Cited

U.S. PATENT DOCUMENTS

| | | | |
|---|---|---|---|
| 3,597,967 | 8/1971 | Drexler | 73/811 |
| 4,165,634 | 8/1979 | Prevorsek et al. | 73/810 |
| 4,574,642 | 3/1986 | Fleischman | 73/799 |
| 5,092,179 | 3/1992 | Freguson | 73/790 |
| 5,275,063 | 1/1994 | Steiger et al. | 73/866 |

FOREIGN PATENT DOCUMENTS

| | | |
|---|---|---|
| 48-95292 | 12/1973 | Japan . |
| 55-13865 | 1/1980 | Japan . |
| 3-95429 | 4/1991 | Japan . |
| 4-113054 | 10/1992 | Japan . |
| 6-281606 | 10/1994 | Japan . |

*Primary Examiner*—Max H. Noori
*Attorney, Agent, or Firm*—Sughrue, Mion, Zinn, Macpeak & Seas, PLLC

[57] ABSTRACT

The major object of this invention is to provide a heat build-up/fatigue measuring method for a viscoelastic body and a hydraulic servo flexometer, that enable direct measurement of a strain (displacement) and a stress (load) applied to a test piece and realize highly precise measurement by controlling the stress and the strain applied to the test piece by hydraulic servo feedback control based on the measured strain and stress.

The hydraulic servo flexometer of this invention includes an upper anvil (22) and a lower anvil (18) having opposing parallel flat surfaces that form test piece holding surfaces, a hydraulic servo cylinder (19) having a piston rod (21) which is coupled to the upper anvil (22) or lower anvil (18) and which actuates in a direction perpendicular to the test piece holding surfaces, and a hydraulic servo mechanism for applying static and dynamic loads to the test piece (23).

8 Claims, 16 Drawing Sheets

BLOCK DIAGRAM OF HYDRAULIC SERVO FLEXOMETER

σ : STRESS
$\sigma_0$ : MAXIMUM DYNAMIC STRESS
δ : PHASE ANGLE DIFFERENCE

ε : STRAIN
$\varepsilon_0$ : MAXIMUM DYNAMIC STRAIN
f : FREQUENCY

HEAT BUILD-UP/FATIGUE MEASURING METHOD FOR VISCOELASTIC BODY AND HYDRAULIC SERVO FLEXOMETER

TECHNICAL FIELD

The present invention relates to a heat build-up/fatigue measuring method for a viscoelastic body and a hydraulic servo flexometer, which measure characteristics associated with heat build-up and fatigue by repeatedly applying a load to a viscoelastic body, e.g., rubber.

BACKGROUND ART

Conventionally, as a test method of evaluating fatigue characteristics associated with heat build-up in a test piece, e.g., vulcanized rubber, by applying dynamic repeated loads to the test piece, ASTM No. D-623-67 Method A is generally used. As a test machine for this purpose, a Goodrich Flexometer which complies with this standard has widely been used.

FIG. 15 shows the schematic arrangement of the conventional Goodrich flexometer used in the above test, the operation of which will be described hereinbelow. Referring to FIG. 15, a rotary motion of a driving shaft 203 driven by a driving motor 201 through a V-shaped pulley 202 is converted into a vertical motion by an eccentric 204 provided to the driving shaft 203. A test piece 210 formed into the shape of a circular cylinder is sandwiched between an upper anvil 211 and a lower anvil 212. A contact 214 of a thermocouple thermally insulated by an ebonite plate 213 is located at the central portion of the lower anvil 212, as shown in FIG. 16. Lead wires 215 extending from this contact 214 are connected to a temperature measurement device 216 to record the temperature of the test piece 210.

Static and dynamic loads are applied to the test piece 210. The compression load of the static load is applied by a balance. Balance weights 222 and 223 are respectively suspended from the two ends of a lever arm 220 of the balance. A load weight 224 having an adjustable weight is placed on the rear balance weight 223. When the load weight 224 is placed, the lever arm 220 tilts to push up the lower anvil 212 which is fixed to the upper surface of the lever arm 220 through an anvil adjustment screw 218 such that its height can be adjusted in the vertical direction. Hence, the compression load is applied to the test piece 210.

A differential transformer 225 is coupled to the rear portion of the lever arm 220. When the lever arm 220 tilts, the amount of its displacement, i.e., the change amount of compression of the test piece 210 is detected by the differential transformer 225. This detection signal is amplified by a motor control circuit (not shown) and converted into a rotation angle of a reversible motor 227. This rotation angle is decelerated by a gear head 228 and converted into a rotation of a rotating shaft, extending in the lever arm 220 in the longitudinal direction, by a worm gear incorporated in the lever arm 220 through an electromagnetic clutch 229. This rotating shaft rotates a helical gear. When the helical gear rotates, the anvil adjustment screw 218 rotates to move the lower anvil 212 in the vertical direction. As a result, the lever arm 220 is always controlled to be horizontal.

After the static load is applied to the test piece 210 in this manner, the eccentric 204 is rotated by the driving motor 201 to move a connecting rod 240 in the vertical direction, thereby moving in the vertical direction a connecting rod plate 242 coupled to the connecting rod 240 through a connecting rod pin 241. A cross bar holding upper anvil 244 is coupled to the connecting rod plate 242 through driving rods 243. When the upper anvil 211 provided in the lower portion vertically moves upon rotation of the driving motor 201, a compression strain (dynamic load) is repeatedly applied to the test piece 210. The amount of displacement of the upper anvil 211, i.e., the amount of deformation of the test piece 210 can be read by a deformation indicator 246 through an indicator rod 245 extending upward from the cross bar 244.

FIG. 17 shows the principle of the Goodrich flexometer described above. As is apparent from FIG. 15, the lever arm 220 can swing at its center and is supported by a knife edge fulcrum 221. The balance weights 222 and 223 each weighing 24 kg are respectively suspended from the two end portions of the lever arm 220 in order to give inertia to the lever arm 220. Furthermore, the load weight 224 is placed on the left balance weight 223 to apply a static load to the test piece 210 from the lower anvil 212 by a lever operation.

When the test piece 210 is strained by the static load to tilt the lever arm 220 to the left, a test piece support 231 connecting the lower anvil 212 and lever arm 220 is lifted upward by a micrometer screw mechanism 230 through rotation of the screw 218 to restore the horizontal state of the lever arm 220. The upper anvil 211 applies a dynamic load, the strain of which has a constant amplitude, to the test piece 210 with an eccentric mechanism. This dynamic load is received by the inertia of the lever arm 220 through the lower anvil 212.

When the fatigue characteristics are to be evaluated based on the above test machine and test method, two types of tests (1) and (2) described below are generally conducted.

(1) A static initial load is applied to the test piece under predetermined temperature conditions. Furthermore, a sinusoidal vibration having a constant amplitude is applied to the test piece. The temperature of heat build-up and the creep amount of the test piece that change over time are measured.

(2) A static initial load is applied to the test piece under predetermined temperature conditions. Furthermore, a sinusoidal vibration having a constant amplitude is applied to the test piece to promote fatigue. The temperature and time at which blow out occurs in the central portion of the test piece are measured.

When a viscoelastic body causes dynamic fatigue, a physical change occurs in the viscoelastic body. This physical change together with heat build-up makes the interior of the viscoelastic body tacky. Volatile substances in the ingredients and the decomposed substance of the viscoelastic body gasify and accumulate in the viscoelastic body. Then, the interior of the viscoelastic body becomes porous so that the gaseous substances finally make a cavity inside the testpiece. This phenomenon is called blow-out.

In particular, in test (2), when measuring the temperature at which blow-out occurs, the test is conducted while applying a vibration to the test piece. The test is stopped when the temperature of heat build-up in the test piece reaches an anticipated value. Then, the test piece is cut into halves, and the blow-out, i.e., the porous state is observed by the human eye. At this time, if blow-out has not occurred, a test is conducted again under the same conditions by using a next test piece. The test is conducted with a higher temperature of heat build-up than the first test. The test piece is divided and observed. Alternatively, if a large number of pores formed by blow-out are observed, the test is conducted by lowering the temperature of heat build-up inversely. Tests are repeated in this manner until the temperature at which blow-out occurs is determined. Accordingly, numerous tests become necessary.

However, the conventional Goodrich flexometer described above depends on a purely mechanical mechanism that applies a static load (load) to the test piece with a lever arm by the principle of a lever, thereby applying a dynamic deformation to the test piece with an eccentric mechanism. For this reason, the knife edge fulcrum that supports the entire inertia acting on the lever arm and the micrometer screw mechanism that requires high precision as it receives all the static and dynamic loads applied to the test piece tend to wear or be damaged. Then, the operating efficiency of the test machine is degraded or a high maintenance cost is required.

The conventional Goodrich flexometer supports the test piece from below with the inertia of the lever arm. If, however, the lever arm is tilted by the static strain of the test piece to delay anvil adjustment with the micrometer screw mechanism, a tilted load is applied to the test piece, disabling accurate measurement.

The conventional Goodrich flexometer measures the static deformation component by mechanical inertia. However, whether the dynamic component is completely removed is doubtful.

The conventional Goodrich flexometer cannot measure dynamic and static stresses (loads) actually applied to the test piece, and regarding deformation of the test piece, it can measure only the average of the dynamic components. Thus, only a macroscopic superficial result can be obtained.

In the conventional heat build-up/fatigue measuring method, since a flexometer which is a mechanical inertial system is employed, measurement can be performed only under the limited conditions that the static load is constant and the dynamic strain has a constant amplitude; a test can only be conducted under conditions that are far different from actual conditions for use. Furthermore, information that are obtained by measurement are temperature rises of the test piece surface caused by internal heat build-up and deformation of the test piece caused by fatigue. However, in the test process, (1) static and dynamic stresses cannot be measured, and (2) regarding deformation, only the average of the dynamic components can be measured.

Therefore, only a macroscopic superficial result can be obtained, and basic data necessary for clarifying the physical mechanism of blow-out, starting with a temperature rise caused by internal heat build-up and reaching destruction, cannot be measured, which is a defect in terms of principle.

In measurement of blow-out, since observation is performed by the human eye by dividing the test piece, the same test must be repeatedly performed from the beginning until blow-out is confirmed by exchanging the test piece. This requires time and labor, not providing a high measurement efficiency.

In the conventional Goodrich flexometer, supply, testing, and discharge of the test piece must all be performed by the person in charge of measurement. When data is to be obtained by using many test pieces, the person in charge of measurement cannot leave the flexometer, which is a very large burden.

Since the temperature of heat build-up is measured on the surface of the test piece, the accurate internal temperature is not clear. When a dynamic load is applied, the entire flexometer vibrates to disable accurate measurement, leading to a decrease in measurement precision.

The present invention has been made in view of the above problems, and has as its object to provide a heat build-up/fatigue measuring method for a viscoelastic body and a hydraulic servo flexometer which, when evaluating fatigue characteristics associated with internal heat buildup of a viscoelastic body, e.g., vulcanized rubber, by applying dynamic repeated loads to the viscoelastic body, can conduct the test by applying static and dynamic loads to the circular cylindrical test piece always perpendicularly to its axial direction by using a hydraulic servo mechanism.

It is another object of the present invention to provide a highly durable hydraulic servo flexometer which can directly measure the strain (displacement) and stress (load) applied to a test piece, thereby enabling highly precise measurement and which has no portion that may wear or be damaged.

It is still another object of the present invention to provide a hydraulic servo flexometer which, for the purpose of measuring basic data necessary for clarifying the physical mechanism, can conduct the test under the following four conditions:

(1) Changes in static and dynamic components of a stress are measured under the test conditions that the static strain is constant and the dynamic strain has a constant amplitude.

(2) Changes in static component of a stress and in dynamic component of a strain are measured under the test conditions that the static strain is constant and the dynamic stress has a constant amplitude.

(3) Changes in static component of a strain and in dynamic component of a stress are measured under the test conditions that the static stress is constant and the dynamic strain has a constant amplitude.

(4) Changes in static and dynamic components of a strain are measured under the test conditions that the static stress is constant and the dynamic stress has a constant amplitude.

It is still another object of the present invention to provide a heat build-up/fatigue measuring method for a viscoelastic body, which can set test conditions that are close to actual conditions for use in order to evaluate the fatigue characteristics, can obtain many pieces of information, and can predict blow-out from these information without dividing the test piece.

It is still another object of the present invention to provide a hydraulic servo flexometer in which transfer, supply, testing, and discharge of the test piece are automated to decrease the burden on the person in charge of measurement, thus improving the measurement efficiency, and in which measurement precision can also be improved.

DISCLOSURE OF THE INVENTION

The first aspect of the invention is characterized, in a heat build-up/fatigue measuring method for a viscoelastic body which measures heat build-up and/or fatigue of a viscoelastic body, in that a strain or a stress applied to a test piece is detected, and a servo mechanism which applies static and dynamic loads to the test piece is controlled based on the detected strain or stress. In this invention, since the static and dynamic loads are applied to the test piece by using the servo mechanism, test conditions close to actual conditions for use can be set, so that highly precise follow-up control and measurement can be performed.

The second aspect of the invention is characterized, in a hydraulic servo flexometer for measuring heat build-up and/or fatigue of a viscoelastic test piece, by comprising an upper anvil and a lower anvil having opposing parallel flat surfaces that form test piece holding surfaces, a hydraulic servo cylinder having a piston rod which is coupled to the upper anvil or the lower anvil and which moves in a direction perpendicular to the test piece holding surfaces, and a hydraulic servo mechanism for applying static and dynamic loads to the test piece.

The third invention is characterized, in the hydraulic servo flexometer described above, by comprising a strain detector for detecting a strain applied to the test piece, and feedback hydraulic servo control means for controlling the hydraulic servo mechanism based on the detected strain.

The fourth invention is characterized, in the hydraulic servo flexometer described above, by comprising a stress detector for detecting a stress applied to the test piece, and feedback hydraulic servo control means for controlling the hydraulic servo mechanism based on the detected stress.

In the second, third, and fourth aspects of the invention, the structure is simple and has no portion, e.g., a knife edge type fulcrum or a micrometer screw mechanism, that may be worn or damaged by the load applied during measurement. Thus, the measuring unit has high reliability and requires substantially no maintenance cost. Also, since a feedback hydraulic servo system is constituted, highly precise follow-up control and measurement can be performed.

The fifth aspect of the invention is characterized, in the hydraulic servo flexometer described above, by comprising a strain detector for detecting a strain applied to the test piece, a stress detector for detecting a stress applied to the test piece, a test condition selector for selecting a test condition or a combination of test conditions from a static component of the detected strain, a dynamic component of the detected strain, a static component of the detected stress, and a dynamic component of the detected stress, and feedback hydraulic servo control means for controlling the servo mechanism based on the selected test condition. In this invention, connection of a feedback loop can be selected by the test condition selector in accordance with four components, i.e., the static strain component, the dynamic strain component, the static stress component, and the dynamic stress component. Also, measurement can be performed by selecting test conditions with an arbitrary combination. Consequently, data which is necessary for clarifying fatigue characteristics associated with internal heat build-up of, e.g., rubber, due to a large dynamic deformation can be obtained within a region where such data cannot be obtained with the conventional Goodrich flexometer.

The sixth aspect of the invention is characterized, in a heat build-up/fatigue measuring method which measures heat build-up and/or fatigue of a viscoelastic body, in that a strain and a stress applied to a test piece are detected, static and dynamic loads applied to the test piece are controlled by a hydraulic servo mechanism based on the detected strain and stress, a creep amount, a complex modulus, and a loss tangent of the test piece are obtained based on the detected strain and stress, and a time point at which blow-out will occur is predicted based on changes over time of the creep amount, the complex modulus, the loss tangent, and the temperature of heat build-up of the test piece.

The seventh aspect of the invention is characterized, in a heat build-up/fatigue measuring method which measures heat build-up and/or fatigue of a viscoelastic body, in that a strain and a stress applied to a test piece are detected, static and dynamic loads applied to the test piece are controlled by a hydraulic servo mechanism based on the detected strain and stress, a loss tangent of the test piece is obtained based on the detected strain and stress, and a relationship between a minimum value of loss tangent and a time point at which blow-out occurs is obtained in advance, so that the time point at which blow-out occurs is obtained from the minimum value of the loss tangent.

In the sixth and seventh aspects of the invention, since the static and dynamic loads are applied to the test piece by using the hydraulic servo mechanism, the test conditions can be set as follows:

(1) the static strain is constant and the dynamic strain has a constant amplitude
(2) the static strain is constant and the dynamic stress has a constant amplitude
(3) the static stress is constant and the dynamic strain has a constant amplitude
(4) the static stress is constant and the dynamic stress has a constant amplitude Accordingly, conditions that are close to the actual conditions for use can be selected from these combinations. Since the creep amount, the complex modulus, and the loss tangent are obtained from the detection values of the static and dynamic stresses and strains, basic data of viscoelasticity can be measured. Accordingly, a time point at which blow-out will occur is predicted from changes in these data. Since the internal observation of the test piece need not be performed by dividing the test piece, unlike in the conventional case, the number of times of the test can be decreased.

The eighth aspect of the invention is characterized, in a hydraulic servo flexometer for measuring heat build-up and/or fatigue of the viscoelastic body, by comprising an upper anvil and a lower anvil arranged in a thermostatic chamber to oppose each other to sandwich a viscoelastic test piece, a hydraulic servo mechanism for moving the upper anvil or the lower anvil in a vertical direction to apply static and dynamic loads to the test piece, hydraulic servo control means for controlling the hydraulic servo mechanism based on a preset test condition, a temperature detector for measuring a temperature of the test piece, a strain detector for detecting a strain applied to the test piece, and a stress detector for detecting a stress applied to the test piece, and a transfer turret which is arranged between the upper anvil and the lower anvil, has an insertion hole formed therein to receive a test piece inserted therein, is provided with fixing means for holding and fixing the test piece inserted in the insertion hole, and rotates intermittently, a rotary driving unit for rotating the transfer turret, opening means for opening the fixing means, thereby releasing the test piece, and a control unit for controlling the hydraulic servo control means, the rotary driving unit, and the opening means to fix the test piece at a supply position with fixing means, rotating the transfer turret until a test position and releasing the test piece, fixing the test piece again with fixing means after the test, and rotating the transfer turret until a discharge position and release the test piece.

The ninth aspect of the invention is characterized, in the hydraulic servo flexometer of the eighth aspect of the invention, by comprising a sample supply cylinder arranged above the sample supply position of the transfer turret in a vertical direction and having a sample stopper in a lower side wall to be movable in a transverse direction, a vertically movable sample platform arranged vertically below the sample supply cylinder, a stopper driving unit for moving the sample stopper in the transverse direction, a platform driving unit for moving the sample platform in a vertical direction, and a control unit for controlling the stopper driving unit and the platform driving unit to load the sample on the sample platform which has moved upward to a lower end of the sample supply cylinder, and moving the sample platform downward such that the sample is located at a position of the fixing means of the transfer turret.

The tenth aspect of the invention is characterized, in the hydraulic servo flexometer of the eighth aspect of the invention, by comprising a sample discharge port provided vertically below the sample discharge position of the transfer turret, a sample discharge port shutter provided at an inlet of the sample discharge port, a pusher movable in a vertical direction vertically above the sample discharge port, a shutter driving unit for moving the sample discharge port shutter, a pusher driving unit for moving the pusher, and a control unit for controlling the shutter driving unit and the pusher driving unit to open the shutter and to move the pusher downward only when discharging the test piece.

In the eighth, ninth, and tenth aspects of the invention, transfer, supply, testing, and discharge of the test piece are automated in the hydraulic servo flexometer by controlling the respective mechanisms with the control unit, thereby improving the measuring efficiency.

The eleventh aspect of the invention is characterized, in a hydraulic servo flexometer for measuring heat build-up and/or fatigue of the viscoelastic body, by comprising an upper anvil and a lower anvil arranged in a thermostatic chamber to oppose each other to sandwich a viscoelastic test piece, a hydraulic servo mechanism for moving the upper anvil or the lower anvil in a vertical direction to apply static and dynamic loads to the test piece, servo control means for controlling the hydraulic servo mechanism based on a preset test condition, a temperature detector for measuring a temperature of the test piece, a strain detector for detecting a strain applied to the test piece, and a stress detector for detecting a stress applied to the test piece, and in that the temperature detector comprises a vertically movable temperature sensor having a needle-like distal end, temperature sensor driving means for vertically moving the temperature sensor, and a control unit which performs a control operation in accordance with a detection value of the strain detector so that the distal end of the temperature sensor is located at a center of the test piece. In this invention, the deformation amount of the test piece is obtained by the control unit from the detection value of the strain detector, the central position of the test piece in the direction of height is obtained, and the temperature sensor is moved by the temperature sensor driving unit so that the distal end of the temperature sensor always maintains its position. Since the distal end of the temperature sensor is located at the central position of the test piece, accurate temperature measurement can be performed.

The twelfth aspect of the invention is characterized, in a hydraulic servo flexometer for measuring heat build-up and/or fatigue of the viscoelastic body, by comprising an upper anvil and a lower anvil arranged in a thermostatic chamber to oppose each other to sandwich a viscoelastic test piece, a hydraulic servo mechanism for moving the upper anvil or the lower anvil in a vertical direction to apply static and dynamic loads to the test piece, hydraulic servo control means for controlling the hydraulic servo mechanism based on a preset test condition, a temperature detector for measuring a temperature of the test piece, a strain detector for detecting a strain applied to the test piece, and a stress detector for detecting a stress applied to the test piece, and in that the hydraulic servo flexometer is accommodated and fixed in a hollow frame, and a vibration absorbing member is packed in the frame. In this invention, the frame that supports the test portion of the flexometer is made hollow, and the vibration absorbing member is packed in the hollow frame, so that any vibration of the test portion itself is prevented, thereby preventing an increase in measurement error.

The thirteenth aspect of the invention is characterized, in a hydraulic servo flexometer for measuring heat build-up and/or fatigue of the viscoelastic body, by comprising an upper anvil and a lower anvil arranged in a thermostatic chamber to oppose each other to sandwich a viscoelastic test piece, a hydraulic servo mechanism for moving the upper anvil or the lower anvil in a vertical direction to apply static and dynamic loads to the test piece, hydraulic servo control means for controlling the hydraulic servo mechanism based on a preset test condition, a temperature detector for measuring a temperature of the test piece, a strain detector for detecting a strain applied to the test piece, and a stress detector for detecting a stress applied to the test piece, and an air circulation plate arranged on a surface opposing air blowing means of the thermostatic chamber to circulate air along a side wall. In this invention, since the air circulation plate is arranged in the thermostatic chamber, the temperature distribution in the thermostatic chamber is uniformed. Thus, the temperatures of the respective test pieces are uniformed to decrease variations in measurement.

BEST MODE FOR CARRYING OUT THE INVENTION

The preferred embodiments of the present invention will be described in detail with reference to the accompanying drawings.

First Embodiment

Figure 1:
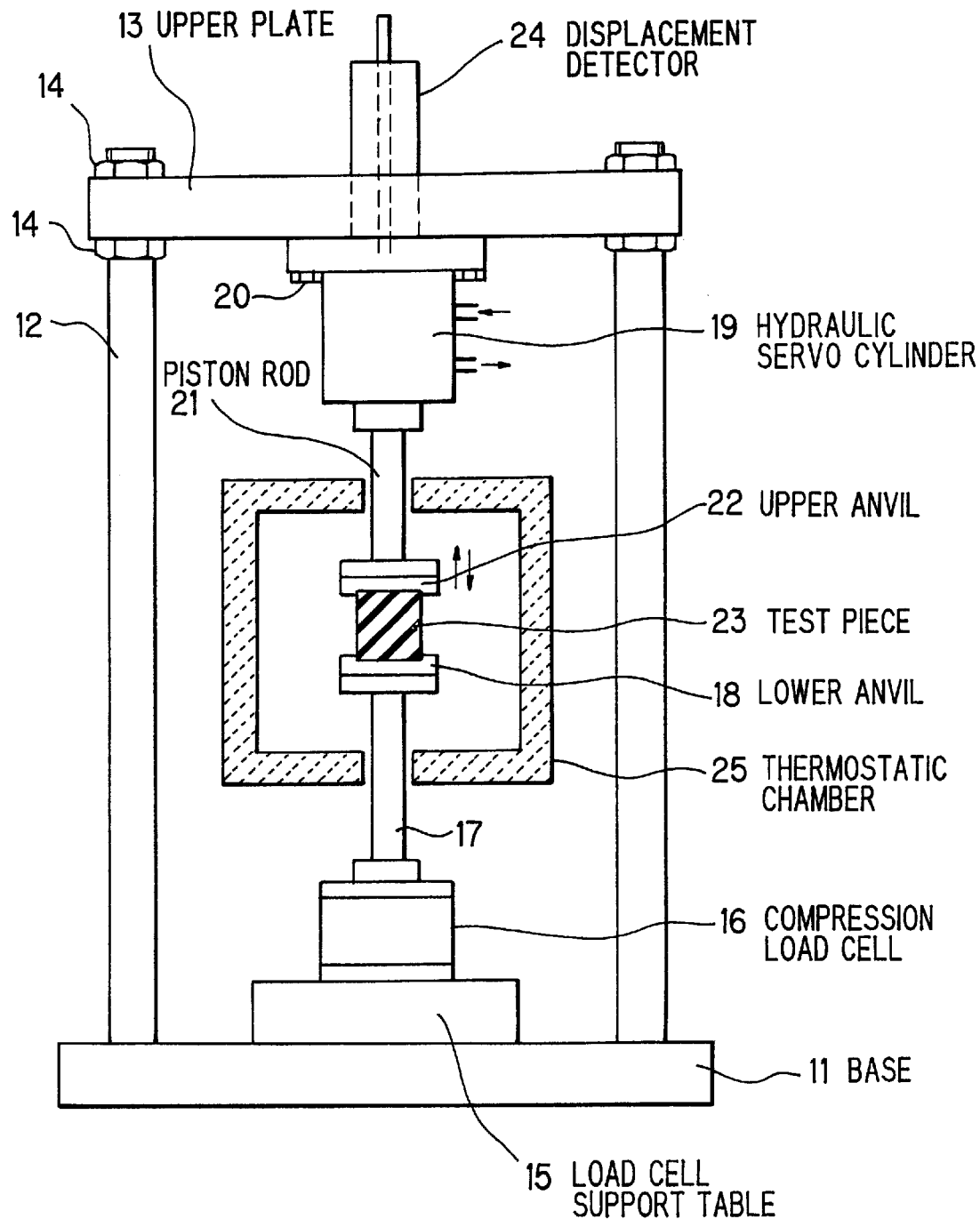
FIG. 1 is a partially sectional side view showing the arrangement of a hydraulic servo flexometer body according to the first embodiment of the present invention.

FIG. 1 is a partially sectional view showing the arrangement of a hydraulic servo flexometer body according to the first embodiment, which employs a heat build-up/fatigue measuring method for a viscoelastic body according to the present invention.

Referring to FIG. 1, reference numeral 11 denotes a base; 12, a support column; 13, an upper plate; 14, nuts; 15, a load cell support table; 16, a compression load cell; 17, a lower anvil connecting rod; 18, a lower anvil; 19, a hydraulic servo cylinder; 20, a fixing bolt for the hydraulic servo cylinder; 21, a piston rod; 22, an upper anvil; 23, a test piece; 24, a displacement detector; and 25, a thermostatic chamber, respectively.

The base 11 is horizontally installed on the floor surface of a measurement room, and four support columns 12 extend vertically upward from the four corners of the substantially square base 11. The upper end portion of each support column 12 forms a screw to which the substantially square upper plate 13 is horizontally attached with two nuts 14. The load cell support table 15 is placed on the upper surface of the base 11, and the compression load cell 16 for detecting a stress applied to the test piece is placed on the load cell support table 15. The lower anvil 18 is fixed to the upper portion of the compression load cell 16 through the lower anvil connecting rod 17 extending through the lower surface of the thermostatic chamber 25.

The hydraulic servo cylinder 19 depends from the upper plate 13. The displacement detector 24 for detecting the displacement of the piston is provided to extend upward from the hydraulic servo cylinder 19 through the upper plate 13. The piston rod 21 of the hydraulic servo cylinder 19 extends through the upper surface of the thermostatic chamber 25 and is connected to the upper anvil 22 in the thermostatic chamber 25. The test piece 23 is sandwiched between the upper anvil 22 and the lower anvil 18. The upper anvil 22, the test piece 23, and the lower anvil 18 are adjusted to a predetermined test temperature by the thermostatic chamber 25.

Figure 2:
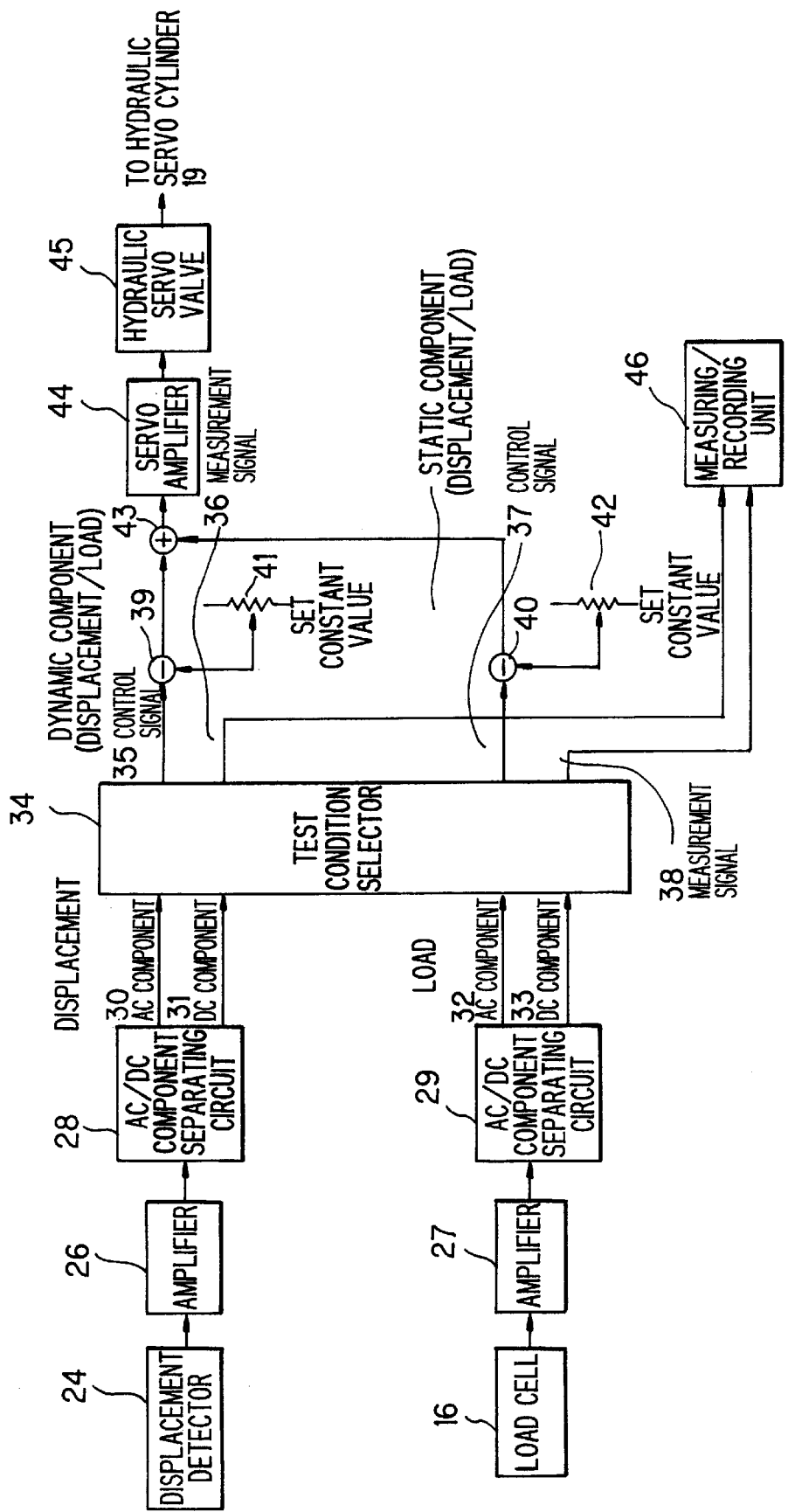
FIG. 2 is a block diagram showing the control circuit of the hydraulic servo flexometer according to the present invention.

FIG. 2 is a block diagram showing the arrangement of a feedback servo control system that controls the hydraulic servo flexometer body described above.

Referring to FIG. 2, reference numeral 24 denotes the displacement detector; 16, the compression load cell; 26 and 27, amplifiers; 28 and 29, AC/DC component separating circuits; 30, the AC component of a displacement signal; 31, the DC component of the displacement signal; 32, the AC component of a stress signal; 33, the DC component of the stress signal; 34, a test condition selector; 35, a dynamic component control signal; 36, a dynamic component measurement signal; 37, a static component control signal; 38, a static component measurement signal; 39 and 40, subtracters; 41 and 42, potentiometers; 43, an adder; 44, a servo amplifier; 45, a hydraulic servo valve; and 46, a measuring/recording unit, respectively.

Referring to FIG. 2, the displacement of a test piece (not shown) is converted into an electric signal by the displacement detector 24, is amplified by the amplifier 26, and is separated into the AC component 30 and DC component 31 of a displacement signal by the AC/DC component separating circuit 28. Similarly, the load (stress) of the test piece is converted into an electric signal by the compression load cell 16, is amplified by the amplifier 27, and is separated into the AC component 32 and DC component 33 of a load signal by the AC/DC component separating circuit 29.

The signals 30 to 33 detected and separated in the above manner are input to the test condition selector 34. A combination of two test conditions are selected from static strain, dynamic strain, static stress, and dynamic stress, and measurement/recording targets are selected from the remaining conditions.

More specifically, the following four conditions can be selected by the test condition selector 34 to conduct the test.

(1) Changes in static and dynamic components of a stress are measured under the test conditions where the static strain is constant and the dynamic strain has a constant amplitude.

(2) Changes in static component of a stress and in dynamic component of a strain are measured under the test conditions where the static strain is constant and the dynamic stress has a constant amplitude.

(3) Changes in static component of a strain and in dynamic component of a stress are measured under the test conditions where the static stress is constant and the dynamic strain has a constant amplitude.

(4) Changes in static and dynamic components of a strain are measured under the test conditions where the static stress is constant and the dynamic stress has a constant amplitude.

The test conditions selected by the test condition selector 34 are extracted as the dynamic component control signal 35 and static component control signal 37, and are respectively input to the subtracters 39 and 40 as minuends. Voltages corresponding to the predetermined values of the test conditions set by the potentiometers 41 and 42 are applied to the subtrahend inputs of the subtracters 39 and 40, respectively. The subtraction results output from the subtracters 39 and 40 are added to each other by the next adder 43 to form a servo control signal. This servo control signal is sent to the servo amplifier 44. The servo amplifier 44 amplifies the servo control signal to drive the hydraulic servo valve 45, thereby controlling the hydraulic pressure supplied to the hydraulic servo cylinder 19. In this manner, the static and dynamic loads complying with the test conditions are applied to the test piece 23 from the piston rod 21 of the hydraulic servo cylinder 19 through the upper anvil 22.

The measurement targets selected by the test condition selector 34 are extracted as the dynamic component measurement signal 36 and static component measurement signal 38, and are recorded by the measuring/recording unit 46.

This embodiment has a simple structure and has no portion, e.g., a knife edge fulcrum or micrometer screw mechanism, that may be worn or damaged by the load applied during measurement. Thus, the measurement unit has a high reliability and requires substantially no maintenance cost. Since a feedback servo system is constituted, highly precise follow-up control and measurement can be performed.

The feedback loop can be connected/switched by the test condition selector among the four conditions, i.e., the static strain component, the dynamic strain component, the static stress component, and the dynamic stress component, and the measurement can be performed by selecting test conditions in arbitrary combinations. Therefore, data necessary for clarifying the fatigue characteristics associated with internal heat build-up of, e.g., rubber, occurring upon large dynamic deformation can be obtained within a region where such data cannot be obtained with the conventional Goodrich flexometer.

Second Embodiment

Figure 3:
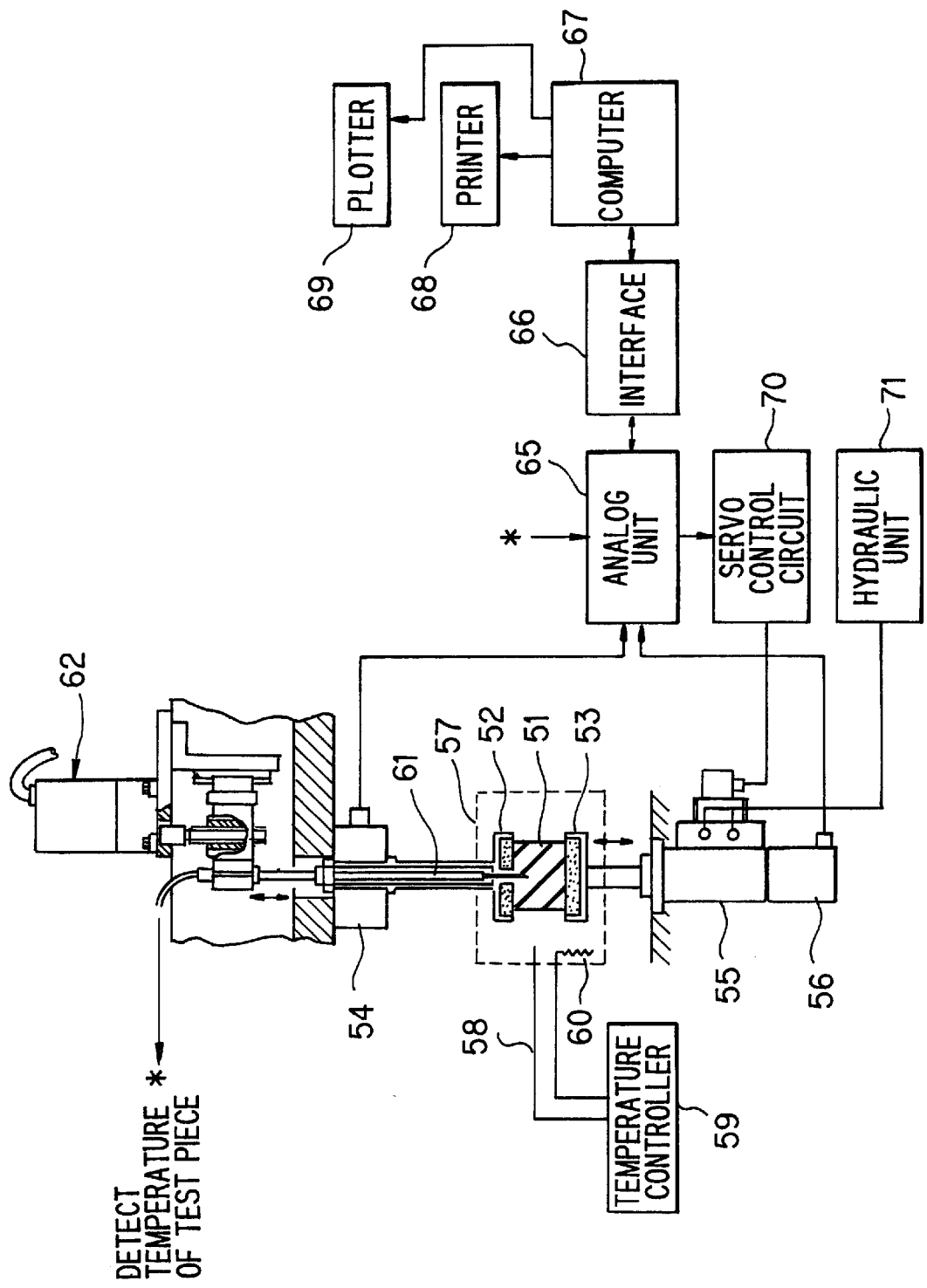
FIG. 3 is a schematic diagram showing a hydraulic servo flexometer according to the second embodiment of the present invention.

FIG. 3 is a schematic diagram showing a hydraulic servo flexometer according to the second embodiment of the present invention. This embodiment provides a hydraulic servo flexometer which measures heat build-up/fatigue characteristics while measuring the temperature of the test piece, thereby predicting a time point at which blow-out will occur.

In the hydraulic servo flexometer of this embodiment, a disk-shaped upper anvil 52 and a disk-shaped lower anvil 53 that vertically sandwich a circular cylindrical test piece 51 are provided to oppose each other. The upper anvil 52 is directly coupled to a load cell 54 serving as a stress detector provided above it, through a rod. The lower anvil 53 is directly coupled to a hydraulic servo cylinder 55 of a hydraulic servo mechanism which is provided below it, through a rod. Furthermore, the hydraulic servo cylinder 55 is directly coupled to a differential transformer 56 serving as a strain detector. The upper anvil 52 and lower anvil 53 are accommodated in a thermostatic chamber 57. The temperatures of the upper anvil 52 and lower anvil 53 are held and controlled to a predetermined value by a heater 60 of a temperature controller 59 while they are detected by a thermocouple 58. The central portion of the upper anvil 52 including the load cell 54 forms a hollow portion, and a temperature sensor 61 having a needle-like distal end is inserted in this hollow portion. A temperature sensor inserting servo motor 62 is controlled such that the distal end of the temperature sensor 61 is always located at the center of the test piece 51 in the direction of height in accordance with the deformation of the test piece 51 in the direction of height.

Values detected by the load cell 54, the differential transformer 56, and the temperature sensor 61 are input to a computer 67 through an analog unit 65 and an interface 66, and the measurement results are output to a printer 68 or a plotter 69. The computer 67 is connected to a servo control circuit 70 through the interface 66 and the analog unit 65 to control the hydraulic servo cylinder 55. The hydraulic servo cylinder 55 is actuated and stopped by a hydraulic unit 71.

The operation of this hydraulic servo flexometer will be described. The circular cylindrical test piece 51 is arranged between the upper anvil 52 and lower anvil 53 to be sandwiched between them, and the interior of the thermostatic chamber 57 is held at the measurement temperature. The servo control circuit 70 controls the hydraulic servo cylinder 55 under test conditions set by the computer 67, to apply predetermined static and dynamic loads to the lower anvil 53. In this manner, the predetermined static and dynamic loads are applied to the test piece through the lower anvil 53. At this time, the static and dynamic strains of the test piece are detected by the differential transformer 56 directly coupled to the hydraulic servo cylinder 55, and the static and dynamic stresses of the test piece are detected by the load cell 54 directly coupled to the upper anvil 52. The temperature of the test piece 51 is detected by the temperature sensor 61. These detection values are input to the computer 67 through the analog unit 65 and interface 66, as described above, to calculate the creep amount, the complex modulus, and the loss tangent. The calculated creep amount, the complex modulus, and the loss tangent are output to the printer 68 or the plotter 69. Based on these detection values of the strains and stresses, the servo control circuit 70 controls the hydraulic servo cylinder 55 to comply with the predetermined test conditions.

In the hydraulic servo flexometer of this embodiment, a hydraulic servo mechanism is employed as the static and dynamic load means, and the feedback servo control system is constituted by combining the differential transformer as the strain detector and the load cell as the stress detector, in the same manner as in the first embodiment. Thus, measurement in accordance with condition setting which varies very much can be performed with a very simple mechanism.

Since the hydraulic servo mechanism is employed, the following mechanical advantages are obtained.

(1) The hydraulic servo flexometer has no portion that may wear or be damaged upon application of an excessive load.

(2) The structure is simple.

(3) Control can be performed freely with reference to both displacement and stress.

(4) Since a feedback servo system can be constituted, highly precise follow-up control and measurement can be performed.

Furthermore, measurement can be performed under the following four conditions so that test conditions that are close to actual conditions for use can be set.

(1) Changes in static and dynamic components of a stress are measured under the test conditions where the static strain is constant and the dynamic strain has a constant amplitude.

(2) Changes in static component of a stress and in dynamic component of a strain are measured under the test conditions where the static strain is constant and the dynamic stress has a constant amplitude.

(3) Changes in static component of a strain and in dynamic component of a stress are measured under the test conditions where the static stress is constant and the dynamic strain has a constant amplitude.

(4) Changes in static and dynamic components of a strain are measured under the test conditions where the static stress is constant and the dynamic stress has a constant amplitude.

Among the above test methods, the measurement contents of items (3) and (4) will be described in detail.

Figure 4:
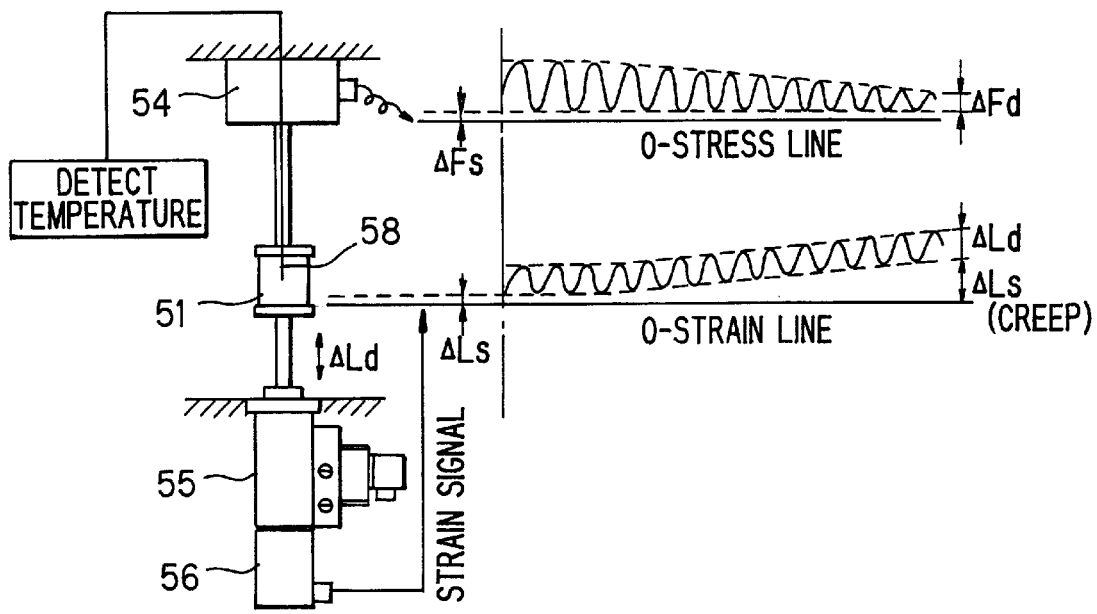
FIG. 4 is an explanatory diagram of measurement done by using this hydraulic servo flexometer.

Test method (3) will first be described. FIG. 4 is a diagram for explaining measurement with test method (3). Although this is a test method that allows measurement even with the conventional Goodrich flexometer, how to apply the static stress and dynamic strain differs largely. While a constant initial load (stress) $\Delta Fs$ applied to the test piece 51 is always maintained by the hydraulic servo cylinder 55 based on the detection value of the load cell 54, a constant sinusoidal amplitude (strain) $\Delta Ld$ is applied to the test piece 51 based on the detection value of the differential transformer 56, to promote fatigue of the test piece 51. When the test piece 51 generates heat, it promotes dynamic fatigue simultaneously, so that its internal stress decreases and its sinusoidal stress $\Delta Fd$ also decreases. Since the constant initial load $\Delta Fs$ is always applied to the test piece 51 together with the sinusoidal stress $\Delta Fd$, an initial strain $\Delta Ls$ increases. This initial strain $\Delta Ls$ is traced as the creep amount, and simultaneously the temperature of heat build-up in the test piece 51 is also measured by the temperature sensor 61.

Figure 5:
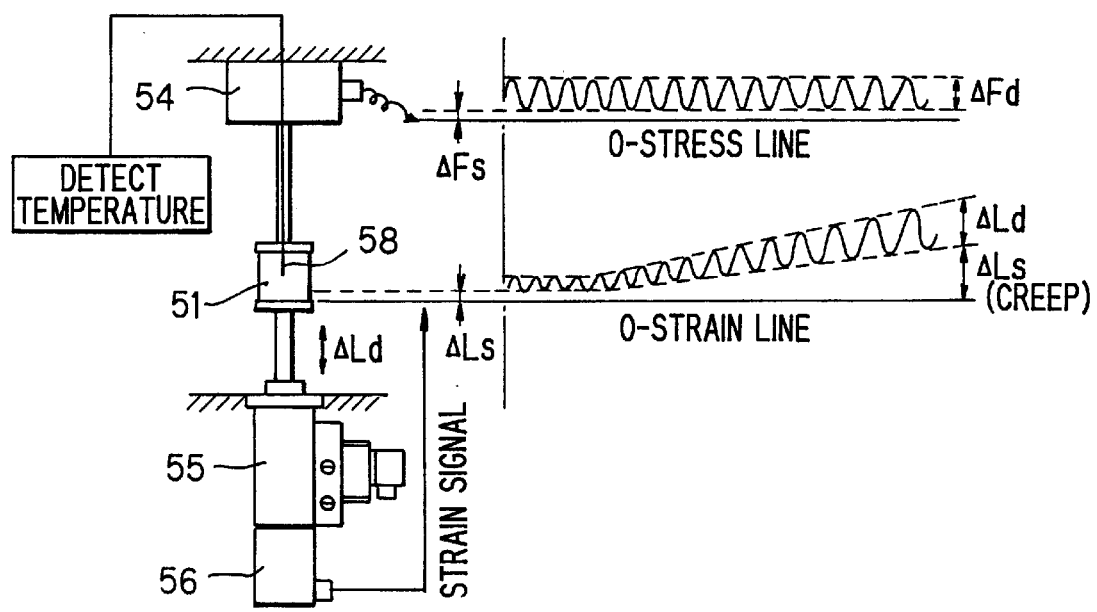
FIG. 5 is an explanatory diagram of another measurement done by using this hydraulic servo flexometer.

FIG. 5 is a diagram for explaining measurement with test method (4). This test is enabled by a hydraulic servo flexometer. When a constant initial load $\Delta Fs$ (detected by the load cell 54) is applied to the test piece 51, a static initial strain $\Delta Ls$ (detected by the differential transformer 56) is generated in the test piece 51. During the test, $\Delta Fs$ is always maintained at the constant value by the hydraulic servo cylinder 55, and a sinusoidal amplitude (strain) $\Delta Ld$ is applied to the test piece 51 such that the sinusoidal stress $\Delta Fd$ of the test piece 51 becomes always constant. When the test piece 51 generates heat, it promotes dynamic fatigue simultaneously, so that its internal stress decreases. Since the sinusoidal amplitude is controlled so that a constant stress is always applied, the amplitude (strain) $\Delta Ld$ increases as the internal stress decreases. Since the constant initial load $\Delta Fs$ is always applied to the test piece 51 together with the amplitude ΔLd, the initial strain ΔLs increases. This initial strain ΔLs is traced as the creep amount, and simultaneously the temperature of heat build-up by the test piece 51 is also measured by the temperature sensor 61.

In any of the above four test conditions, static and dynamic stresses and strains are applied by the hydraulic servo cylinder, and the initial strain (creep amount) ΔLs and the sinusoidal strain ΔLd are detected by the differential transformer and the sinusoidal stress ΔFd is detected by the load cell.

Figure 6:
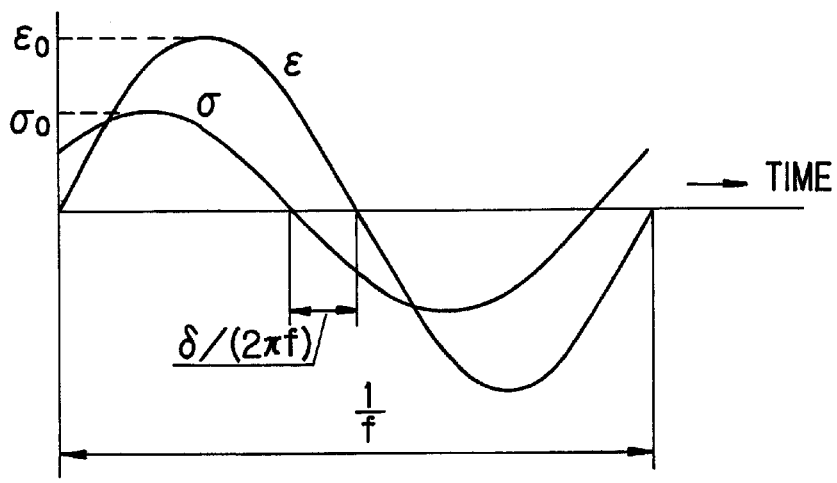
FIG. 6 is a graph showing the sinusoidal waveforms of strain and stress.

A loss tangent tanδ can be obtained from the sinusoidal strain ΔLd and sinusoidal stress ΔFd. FIG. 6 is a graph for explaining the waveforms of these strain and stress. If the test piece is a viscoelastic body, the waveform of the sinusoidal strain ΔLd has a phase difference corresponding to an angle δ from the waveform of the sinusoidal stress ΔFd. The tangent of the phase angle δ is called the loss tangent tanδ, which represents the magnitude of the viscoelastic element. As the tangent δ increases, the viscosity increases; as it decreases, the viscosity decreases so that the viscoelastic body becomes close to an elastic body.

In this system, since the sinusoidal strain and stress applied to the test piece are detected simultaneously, the dynamic viscoelasticity can be calculated in accordance with the following equation.

When a sinusoidal strain $\epsilon$ having an amplitude $\epsilon_0$ is applied to the test piece, the sinusoidal strain is given by:

$$\epsilon = \epsilon_0 e^{i\omega t} \quad (1)$$

where t: time, e: the base of natural logarithm, and ω: the angular frequency.

At this time, the phase of the stress δ generated in the test piece advances by δ, as shown in FIG. 6. The stress at this time is a complex number consisting of a component in phase with the strain and a component having a phase lead of π/2 with respect to the strain.

An elastic modulus E is defined as the ratio of stress to strain, and is given in the form of a complex number in accordance with the following equation (2):

$$\sigma = E^* \cdot \epsilon = (E' + iE'')\epsilon \quad (2)$$

where
 i: an imaginary unit (i=$\sqrt{-1}$),
 E': the dynamic storage modulus, and
 E": the dynamic loss modulus
 The loss tangent δ is given by:
ti tanδ=E"/E'+tm (3)

In measurement of changes in dynamic viscoelasticity upon changes in temperature, when E', E", and tanδ are calculated as a function of the temperature of heat build-up by the test piece while setting the frequency at a constant value, transition, relaxation phenomena, and the like can be determined from the variance of E' and absorption of E". The blow-out temperature can be predicted and the fatigue mechanism can be analyzed by analyzing the transition, the relaxation phenomena, and the like.

Figure 7:
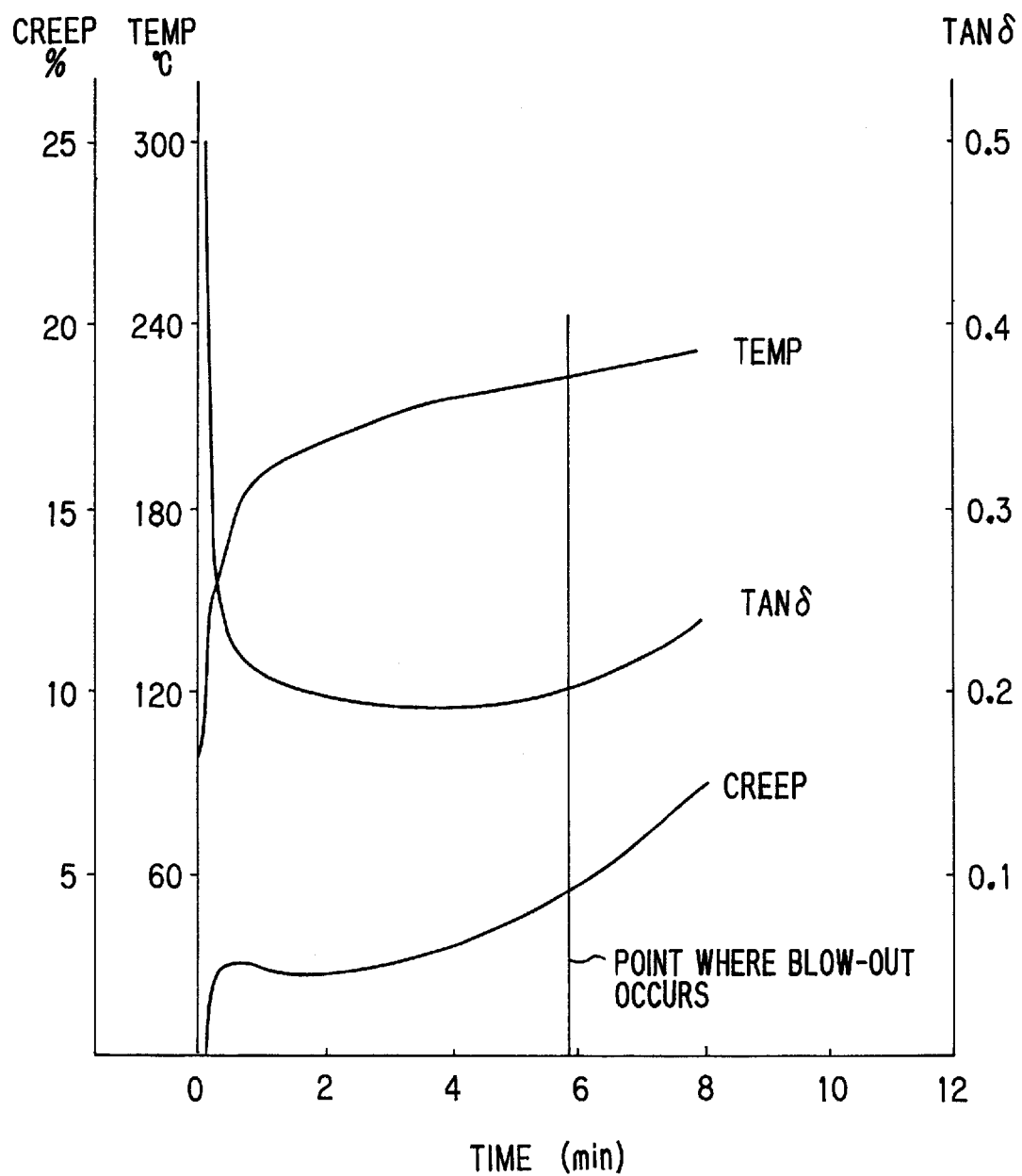
FIG. 7 is a graph of measurement data indicating the relationship among the heat build-up temperature, the creep amount, and the loss tangent.

FIG. 7 shows the characteristics curves of the fatigue test of a tire rubber obtained by measurement with test method (4). Test method (4) is selected because its conditions are close to the conditions for use of the tire. More specifically, in a vehicle tire, the initial load (stress) is the pneumatic pressure, the dynamic stress having a constant amplitude is the weight of the vehicle, and the frequency is the driving speed. In the case of an actual tire, a decrease in stress of the dynamic strain does not occur. Accordingly, test method (4) in which a constant initial stress and a sinusoidal stress having a constant amplitude are applied to the test piece is appropriate as the test condition.

The test of the test piece was started at an initial temperature of 100° C. After the start of the test, the temperature of heat build-up and the creep amount increase sharply and the loss tangent tanδ decreases sharply, and then they stabilize slightly. When a point where blow-out occurs is obtained by dividing the test piece and visually inspecting the interior of the test piece, as in the conventional case, blow-out starts to occur at a time point where the loss tangent has slightly increased from its minimum value. In the case of the test piece made of such a material, it was found out that a predetermined relationship was established between the minimum value of the loss tangent tanδ and the point where blow-out occurred. Therefore, if an equation defining this relationship is obtained in advance, the time point at which blow-out occurs can be obtained from the minimum value of the loss tangent tanδ, and the temperature of heat build-up by the test piece and the creep amount of the test piece at this time can also be obtained.

Although the above case is merely an example, the fatigue characteristics of a viscoelastic body in actual use can be obtained since the measurement signals of both strain and stress can be obtained as electric signals with a high resolution at a high speed under test conditions close to the actual conditions for use. In particular, since the creep amount, the complex modulus, and the loss tangent can be obtained from the detected values of the strain and stress, data necessary for clarifying blow-out can be obtained, thus enabling prediction of blow-out. As compared to conventional detection of blow-out by visual observation through division, the number of samples can be decreased. Also, since the time point at which blow-out occurs can be obtained by calculation, variations according to the skill of the person in charge of measurement can be prevented. Also, since a test can be performed such that the dynamic stress amplitude becomes constant, a hard viscoelastic body that cannot be tested with the conventional Goodrich flexometer can be tested.

Third Embodiment

Figure 8:
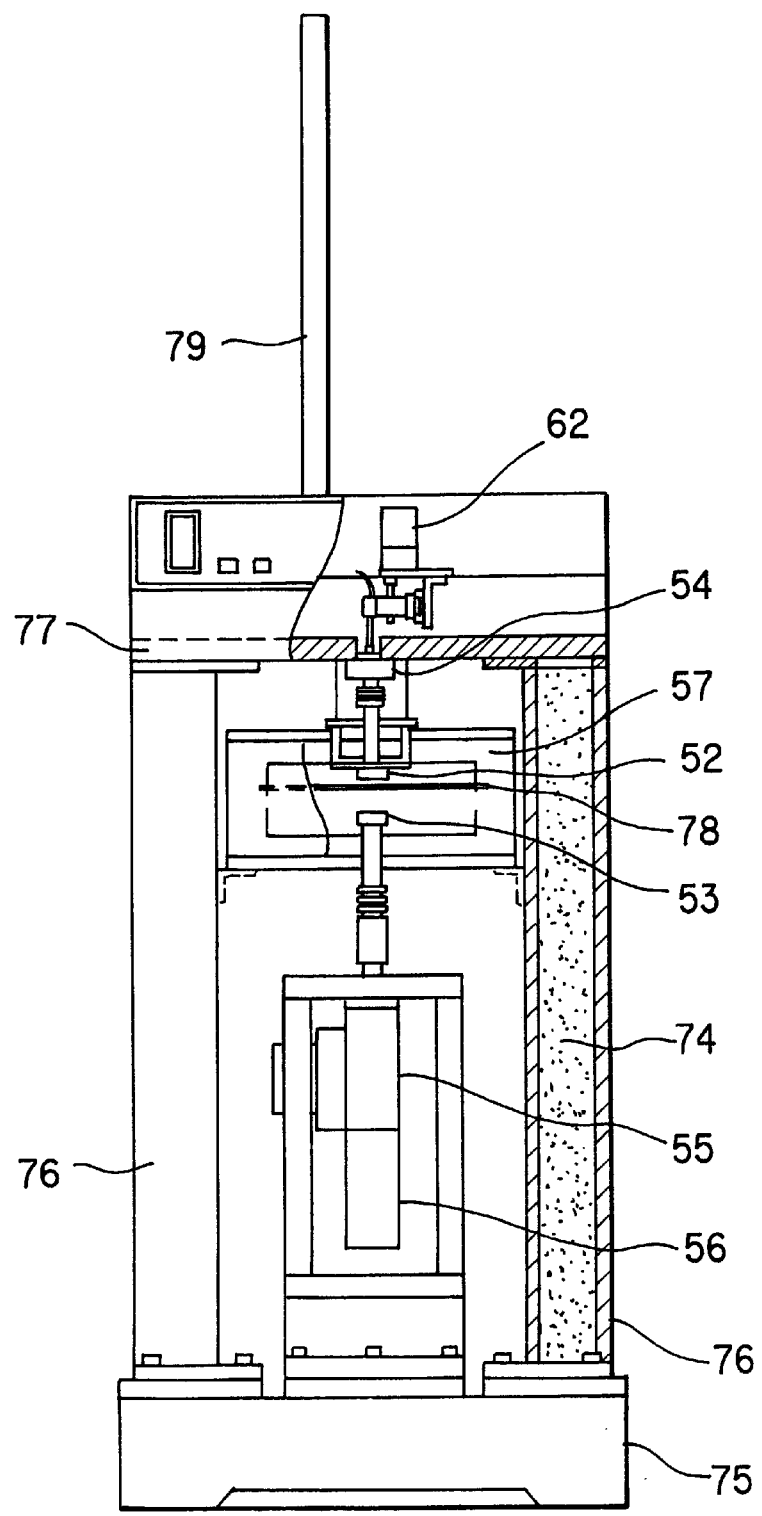
FIG. 8 is a diagram showing a hydraulic servo flexometer according to the third embodiment of the present invention.

FIG. 8 shows the entire arrangement of a hydraulic servo flexometer according to the third embodiment of the present invention. This system is a hydraulic servo flexometer having an automatic measurement mechanism and its basic arrangement is identical to that of the system shown in FIG. 3. Thus, the corresponding portions are denoted by the same reference numerals, and a detailed description thereof will be omitted. The test unit shown in FIG. 3 is incorporated in a central portion surrounded by a base 75 at the lower portion of the main body, two side frames 76, and an upper frame 77. The interiors of the two side frames 76 are hollow and packed with sand 74 as the vibration absorbing material. This aims at preventing vibration of the test unit itself that increases measurement errors.

Both upper and lower anvils 52 and 53 are located at the center of a thermostatic chamber 57, and the systems for supplying, transferring, testing, and discharging a test piece 51 are integrally formed with this thermostatic chamber. The test piece is transferred with a disk-shaped rotatable transfer turret 78 arranged between the upper anvil 52 and the lower anvil 53. A supply cylinder 79 for supplying the test piece is arranged above the transfer turret 78. Although not shown, a discharge port for discharging a test piece that has undergone the test is formed in the rear portion of the thermostatic chamber 57. In this manner, transfer, supply, testing, and discharge of the sample are automated under the control of a computer. The arrangements and operations of the respective portions will be described.

(1) Sample Transfer Mechanism

Figure 9A:
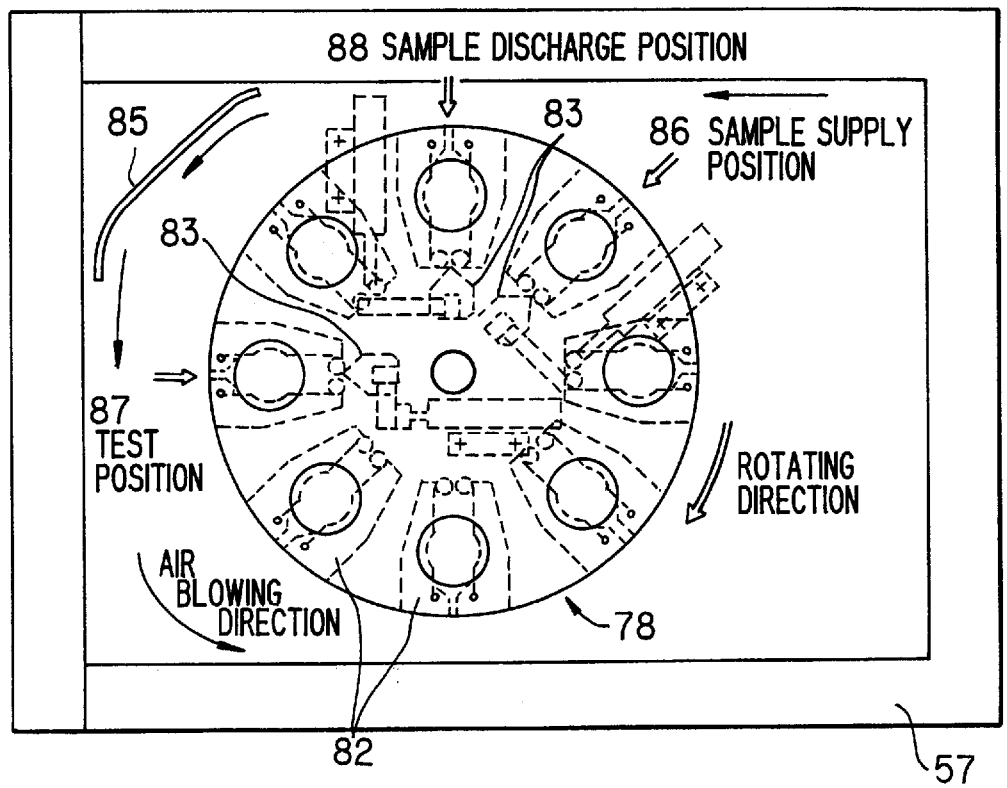
FIG. 9($a$) and FIG. 9($b$) are diagrams showing the transfer turret of the automatic hydraulic servo flexometer shown in FIG. 8.
Figure 9B:
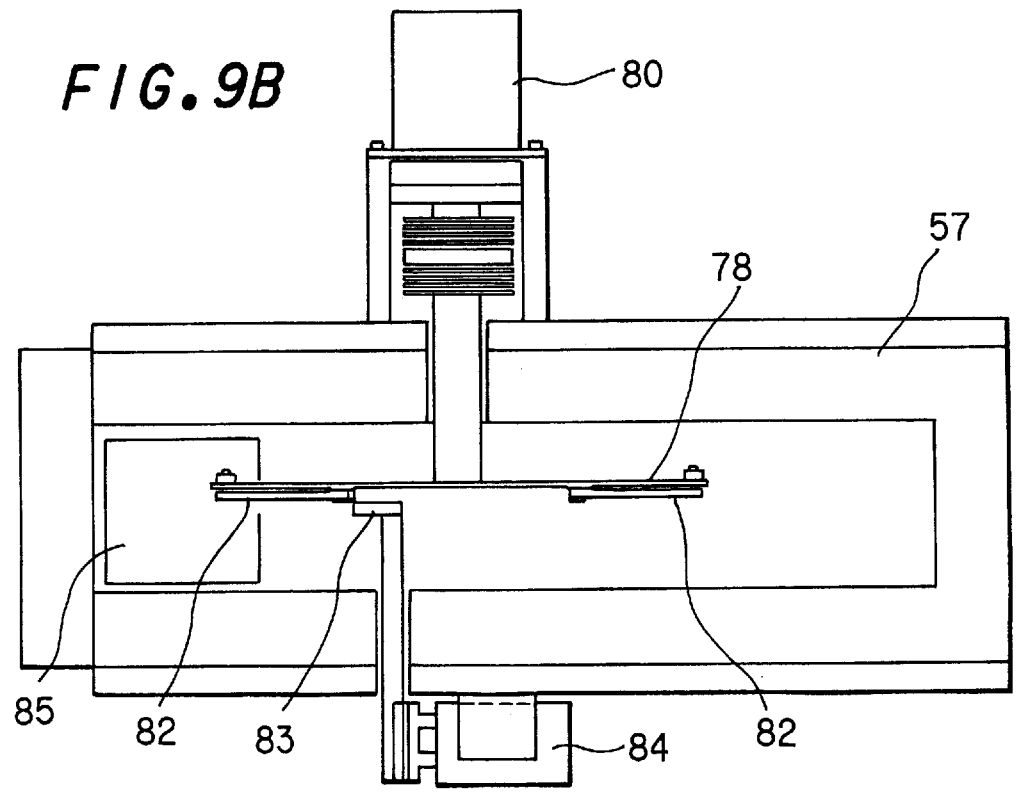

FIG. 9 includes views showing the structure of the sample transfer turret, in which FIG. 9(a) is a plane view, and FIG. 9(b) is a front view. The transfer turret 78 is located at the central portion in the thermostatic chamber 57 and is directly coupled to a turret rotating air cylinder 80 provided on the external upper portion of the thermostatic chamber 57. The turret rotating air cylinder 80 rotates 45° per motion, and rotates intermittently under the control of pneumatic valves. The transfer turret 78 has eight test piece insertion holes to which clamps 82 are attached respectively. The clamps 82 for fixing and holding the test pieces 51 are normally closed with springs and opened upon operation of clamp releases 83 provided at three predetermined positions. The clamp releases 83 are driven by clamp release air cylinders 84. The operating positions of the transfer turret 78 where the clamps 82 are opened/closed are fixed, which are three, i.e., a sample supply position 86, a sample measurement position 87, and a sample discharge position 88. A clamp release 83 and a clamp release air cylinder 84 are mounted for each of the three positions. The turret rotating air cylinder 80 and the clamp release air cylinders 84 are connected to the computer to be controlled by it.

As the transfer turret 78 is arranged in the thermostatic chamber 57, the temperature in the thermostatic chamber 57 cannot be uniformed easily. Thus, air is blown into the thermostatic chamber 57 to uniform the temperature in it. An air circulation plate 85 is provided so that air can circulate in the thermostatic chamber 57 easily. In this case, air is blown from a deep portion of the thermostatic chamber 57. The air circulation plate 85 is provided obliquely on a corner side of side walls opposing the air-blowing portion, so that air is blown in the circulating direction. Since air circulates in the thermostatic chamber in this manner, the temperature distribution in the thermostatic chamber is uniformed to decrease variations among test pieces. Although one air circulation plate 85 is provided in FIG. 9, a plurality of air circulation plates 85 can be provided.

Figure 10:
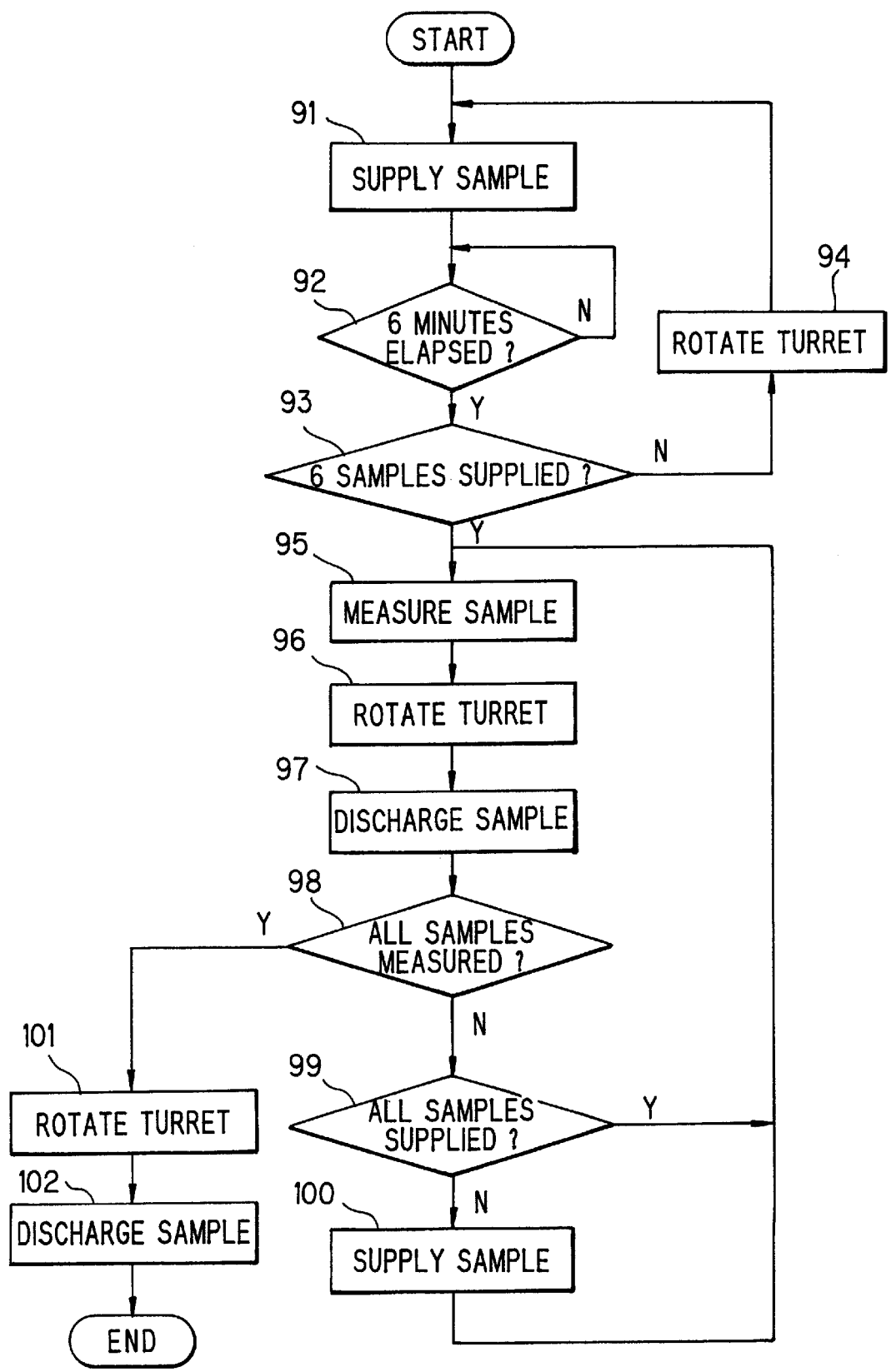
FIG. 10 is a flow chart for explaining the operation of the transfer turret.

The operation of the transfer turret under the control of the computer will be described with reference to the flow chart of FIG. 10. In step 91, a test piece 51 is supplied at the sample supply position 86. The test piece 51 fixed and held by the clamps 82 is transferred by clockwise rotation through 45° by one motion of the turret rotating air cylinder 80, and is stopped. After a lapse of 6 minutes in step 92, the flow advances to step 93, and whether six samples are supplied is checked. If six samples have not been supplied, the flow advances to step 94. The transfer turret rotates through 45°. Then, the flow returns to step 91 to supply a sample. Sample measurement takes about 6 minutes and six samples are supplied to the sample measurement position 87, during which the samples are heated and lagged in the thermostatic chamber 57. The above described loop aims at equalizing the heating and lagging temperature so that all the samples are measured under the same conditions. Accordingly, a sample requires 30 minutes to reach the sample measurement position 87, during which each sample is heated and lagged. Note that if a sample is measured within less than 6 minutes and heated and lagged for less than 30 minutes, this sample is additionally heated and lagged at the measurement position.

When the test pieces 51 that are sequentially supplied and transferred reach the sample measurement position 87, the clamp releases 83 are actuated by the clamp release air cylinders 84 to open the clamps 82. Each test piece 51 is inserted between the upper and lower anvils 52 and 53, and the test is started (step 95). During testing process, five test pieces 51 are present, from one at the sample supply position 86 to one which is before the sample measurement position 87 by one, as they are fixed and held by the transfer turret 78. During this process, these test pieces 51 are heated and lagged at a test temperature set in the thermostatic chamber 57. When the test is completed, the test piece 51 is fixed and held by the clamp 82, and is transferred to the subsequent position by rotation of the transfer turret 78 through 45° (step 96). The test piece 51 waits at this position until the subsequent test piece is tested. When the test is completed, the test piece 51 is transferred to the sample discharge position 88. When the test piece 51 arrives at this position, the clamp release air cylinder 84 is actuated to open the clamp 82, thereby discharging the test piece (step 97).

In step 98, whether all the samples have undergone measurement is checked. If all the samples have not undergone measurement, the flow advances to step 99 to check whether all the samples have been supplied. If all the samples have been supplied, the flow returns to step 95 to perform a measurement. If all the samples have not been supplied, more samples are supplied in step 100, and the flow returns to step 95 to perform a measurement. In step 98, if all the samples have undergone measurement, the flow advances to step 101 to rotate the transfer turret 78, thereby discharging the test pieces 51 remaining on the transfer turret 78 (step 102).

(2) Sample Supply Mechanism

Figure 11:
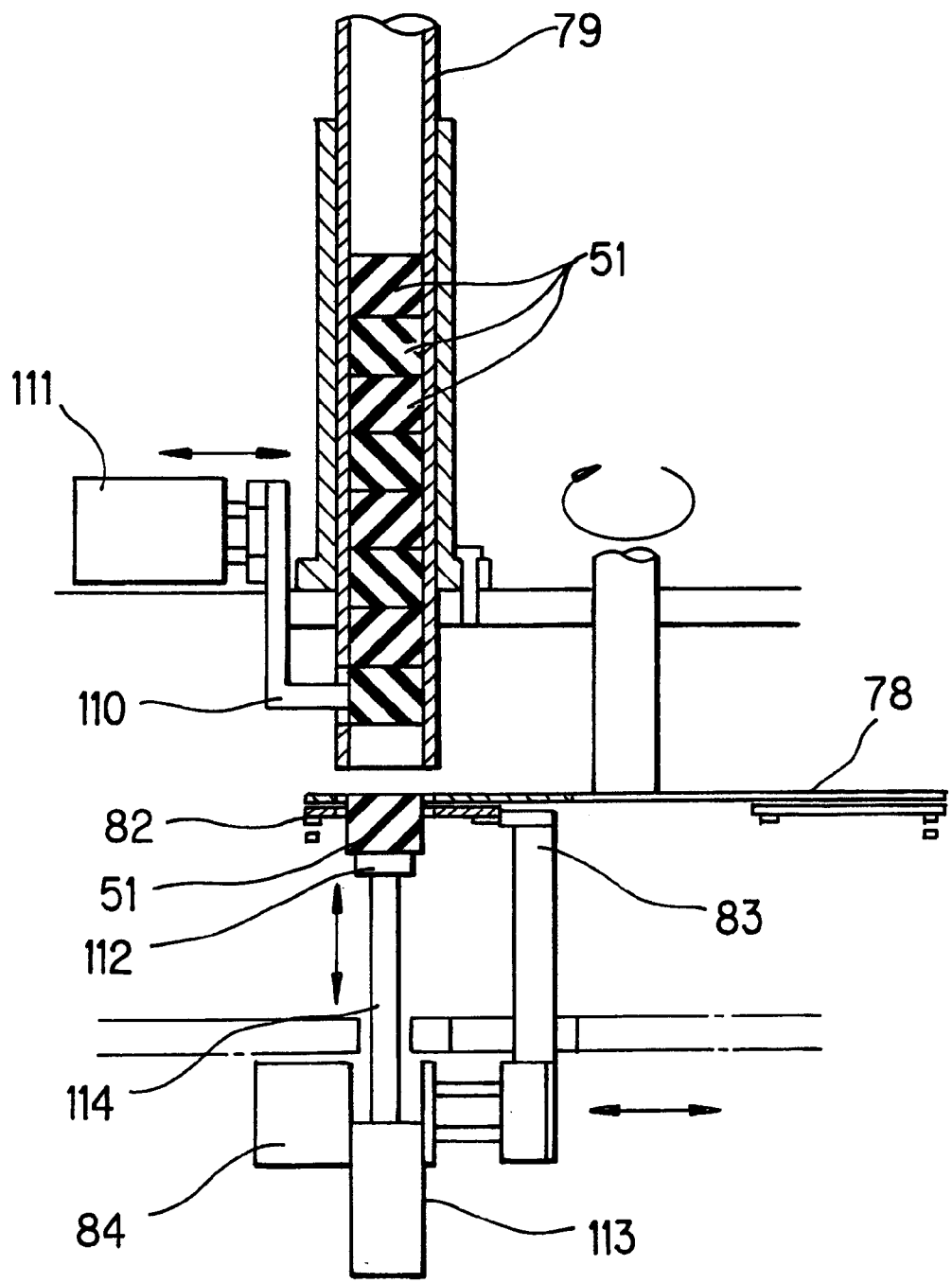
FIG. 11 is a diagram showing the sample supply mechanism of the automatic hydraulic servo flexometer.

As shown in FIG. 8, the sample supply cylinder 79 is provided vertically on the external upper portion of the thermostatic chamber 57, and a supply system is mounted on the vertical extension line of the sample supply cylinder 79. FIG. 11 shows a schematic diagram of the sample supply mechanism.

The test pieces 51 are inserted in the sample supply cylinder 79 from the upper side, so that 40 test pieces 51 are stacked in the sample supply cylinder 79. The lowest test piece 51 is urged by a sample supply stopper 110 to be fixed on the inner wall of the sample supply cylinder 79. The sample supply stopper 110 can be moved in the horizontal direction by a sample supply stopper air cylinder 111. A sample platform 112 is arranged below the vertical extension line of the sample supply cylinder 79, and can be vertically moved by a sample platform air cylinder 113. The sample platform 112 is normally set at the lowest portion of the downward movement of a piston 114. The sample supply stopper air cylinder 111 and the sample platform air cylinder 113 are connected to the computer to be controlled by it.

The operation of this sample supply mechanism will be described.

When the transfer turret 78 rotates and stops at the sample supply position 86, the clamp release air cylinder 84 at the sample supply position 86 is actuated to operate the clamp release 83 at the sample supply position 86, thereby opening the corresponding clamp 82. Subsequently, the sample platform air cylinder 113 is actuated to move the sample platform 112 upward until it comes into contact with the lowest portion of the sample supply cylinder 79, so that the sample platform 112 waits for a test piece 51 to drop. Subsequently, the sample supply stopper air cylinder 111 is actuated to separate the sample supply stopper 110 from the test piece 51, and simultaneously all the test pieces inserted in the sample supply cylinder 79 fall naturally onto the sample platform 112. The sample supply stopper air cylinder 111 is actuated so that the sample supply stopper 110 fixes the subsequent test piece 51 by urging. Thereafter, the sample platform 112 is moved downward, so that the circular cylindrical upper surface of the supply sample moves downward until it is level with the upper surface of the transfer turret 78, and is stopped. Subsequently, the clamp release 83 at the sample supply position 86 is actuated to close the corresponding clamp 82, thereby fixing and holding the test piece. This test sample is tested by the sample measurement position 87, and waits for a subsequent operation as it is held by the clamps 82 until the next instruction is supplied.

(3) Sample Test Mechanism

Figure 12:
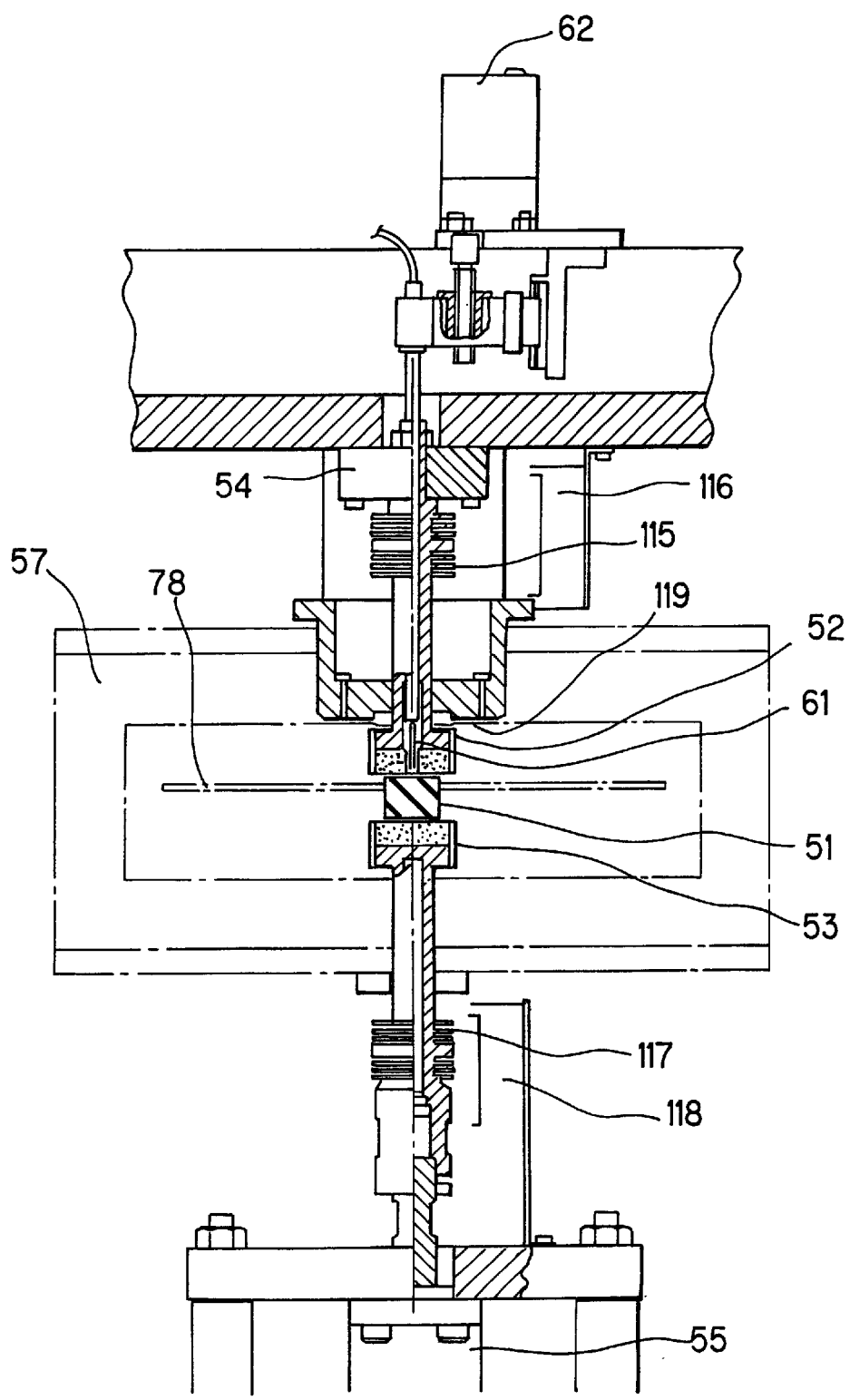
FIG. 12 is a diagram showing the test mechanism of the automatic hydraulic servo flexometer.

The test is started when the test piece 51 is transferred to the measurement start position by the transfer turret 78. FIG. 12 shows the arrangement of this test mechanism. A ceramic member having an excellent heat insulating effect is inserted in the lower anvil 53 at the distal end portion of the piston side rod directly coupled to the piston rod of the hydraulic servo cylinder 55. The ceramic heat-insulating member of the lower anvil 53 is incorporated so that the temperature of heat build-up in the test piece is not conducted to the metal rod. On the upper side of the test piece, the upper anvil 52 is also integrally formed with the load cell 54 side rod, and this rod is fixed to the load cell 54 by screwing. The rod of the upper anvil 52 including the load cell 54 has a hollow central portion, and the temperature sensor 61 having a needle-like distal end is inserted in this hollow central portion from above the test piece toward the central portion of the test piece before the start of the test, in order to measure the temperature of heat build-up in the test piece 51 during the test. The rods of the upper and lower anvils 52 and 53 have radiation fins 115 and 117, respectively, which are respectively cooled by air-cooling fans 116 and 117 so that the heat will not be conducted to the piston side and load cell side. A transverse vibration preventing mechanism fixed by a plate-shaped cross spring 119 is incorporated so that any transverse vibration of the upper anvil 52 is prevented during the test.

The operation of the test mechanism will be described. When the test piece 51 reaches the sample measurement position 87, the lower anvil 53 moves upward and stops where the upper surface of the test piece 51 comes into contact with the ceramic surface of the upper anvil 52. The clamp 82 opens, and the test piece 51 stabilizes at the centers of the upper and lower anvils 52 and 53. The needle-like temperature sensor inserting mechanism is actuated to insert the needle-like temperature sensor 61 to the central portion of the test piece 51 from above. Then, the test is started, and the lower anvil 53 moves upward until it applies an initial load set by the computer to the test piece. The initial load applied to the test piece 51 is detected by the load cell 54 and is fed back to the servo mechanism to control the upward movement of the lower anvil 53. In this fashion, the test piece 51 deforms by a degree corresponding to the initial load.

Figures 13A, 13B, 13C:
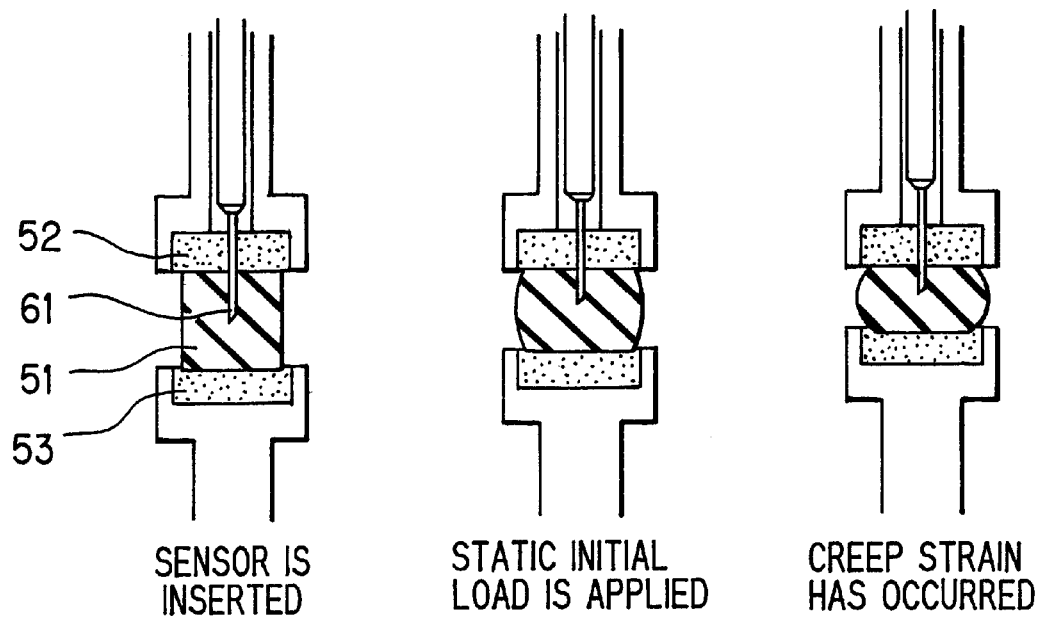
FIGS. 13($a$) to 13($c$) are views for explaining the operation of a temperature sensor.

Regarding the mechanism for inserting the temperature sensor 61 into the test piece 51, the computer is connected to the temperature sensor inserting servo motor 62 to control it. FIG. 13 includes views for explaining the operation of the needle-like temperature sensor. As shown in FIG. 13(a), the distal end portion of the needle-like temperature sensor 61 which is inserted into the test piece 51 at the start of the test is inserted to a depth corresponding to the central portion of the test piece 51. When an initial load is applied to the test piece to deform it, the temperature sensor 61 is controlled by the computer from the detection value of the differential transformer so that the depth of its needle-like distal end portion is located at the center of the deformed test piece 51. Thus, even if the fatigue of the test piece 51 progresses and the test piece deforms largely, as shown in FIGS. 13(b) and 13(c), the needle-like temperature sensor 61 is controlled by the servo mechanism such that its distal end portion is constantly located at the center of the test piece 51, thus allowing accurate measurement of the temperature of heat build-up in the test piece 51.

When the temperature sensor 61 is inserted in the test piece 51, the lower anvil 53 applies a sinusoidal amplitude and frequency preset by the computer to the test piece 51, thus starting the test. The vibration is maintained until the test period preset by the computer ends. When the test ends, the vibration of the lower anvil 53 is stopped. The test piece 51 is held between the upper and lower anvils 52 and 53 in the deformed state. In this state, the clamp release 83 at the sample measurement position 87 is actuated to close the corresponding clamp 82, thereby fixing and holding the test piece 51. Thereafter, the lower anvil 53 moves downward to a predetermined position and stops. When all the operations of the test end, the transfer turret 78 rotates through 45° to transfer the subsequent test piece 51 to a position between the upper and lower anvils 52 and 53 to wait for the subsequent test. When the transfer turret 78 stops, the discharge operation of the test piece 51 that has reached the sample discharge position 88 and the sample supply operation progress simultaneously.

(4) Sample Discharge Mechanism

Figure 14:
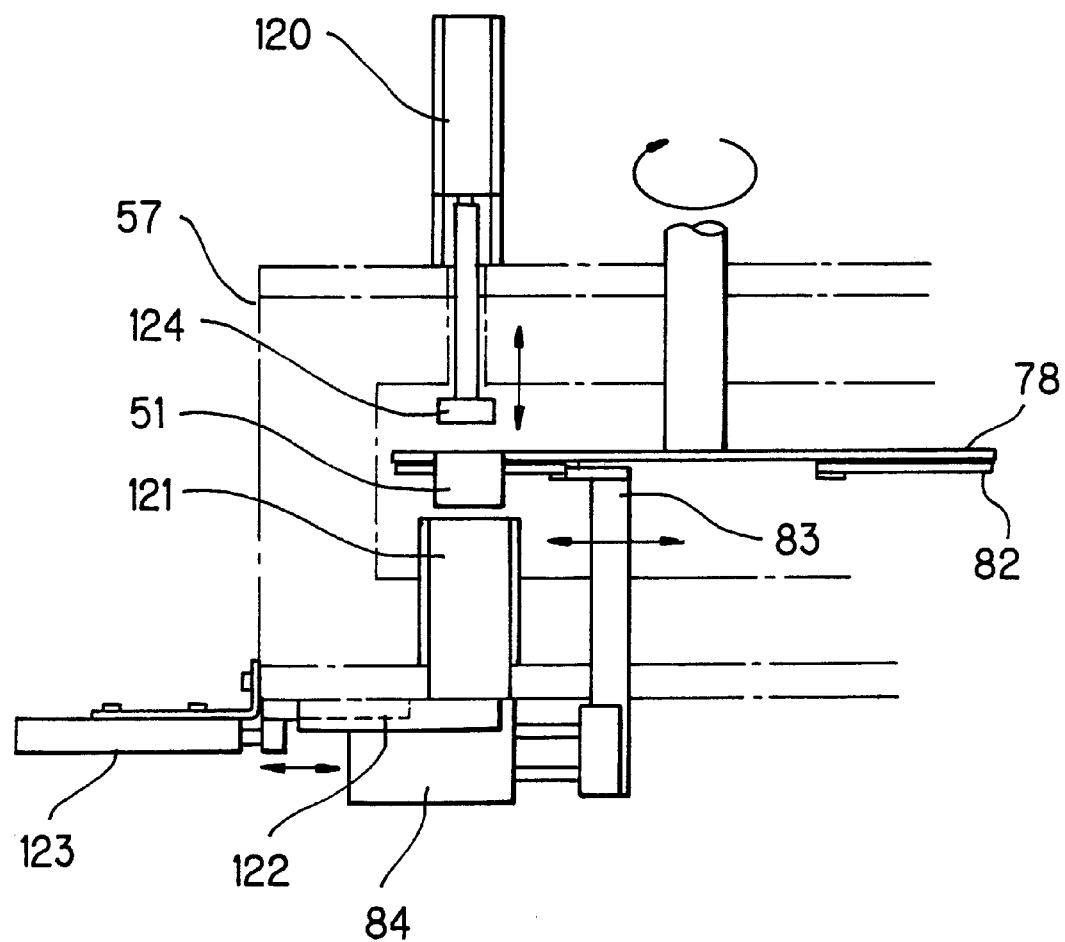
FIG. 14 is a diagram showing the sample discharge mechanism of the automatic hydraulic servo flexometer.
Figure 15:
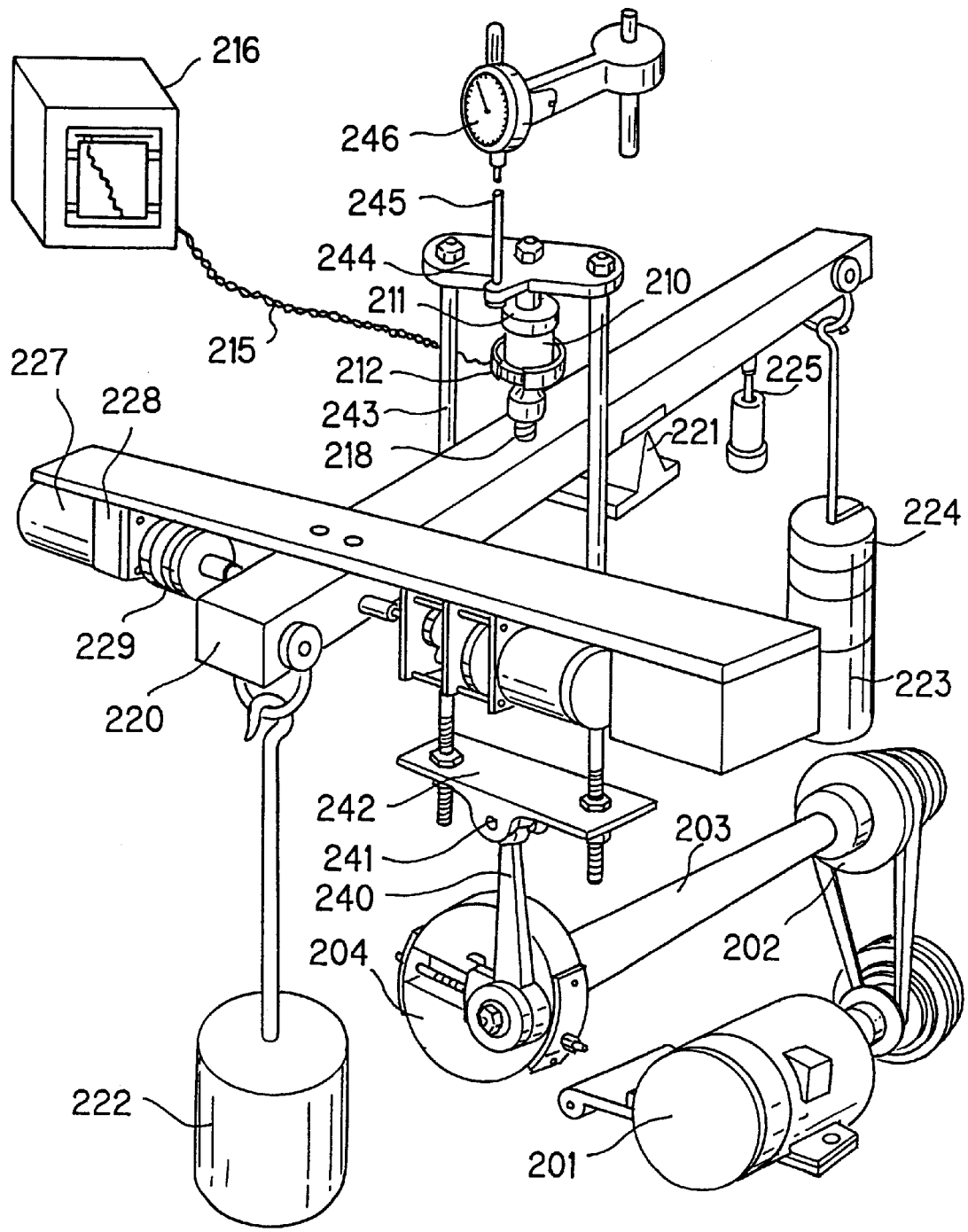
FIG. 15 is a diagram showing a conventional Goodrich flexometer.
Figure 16:
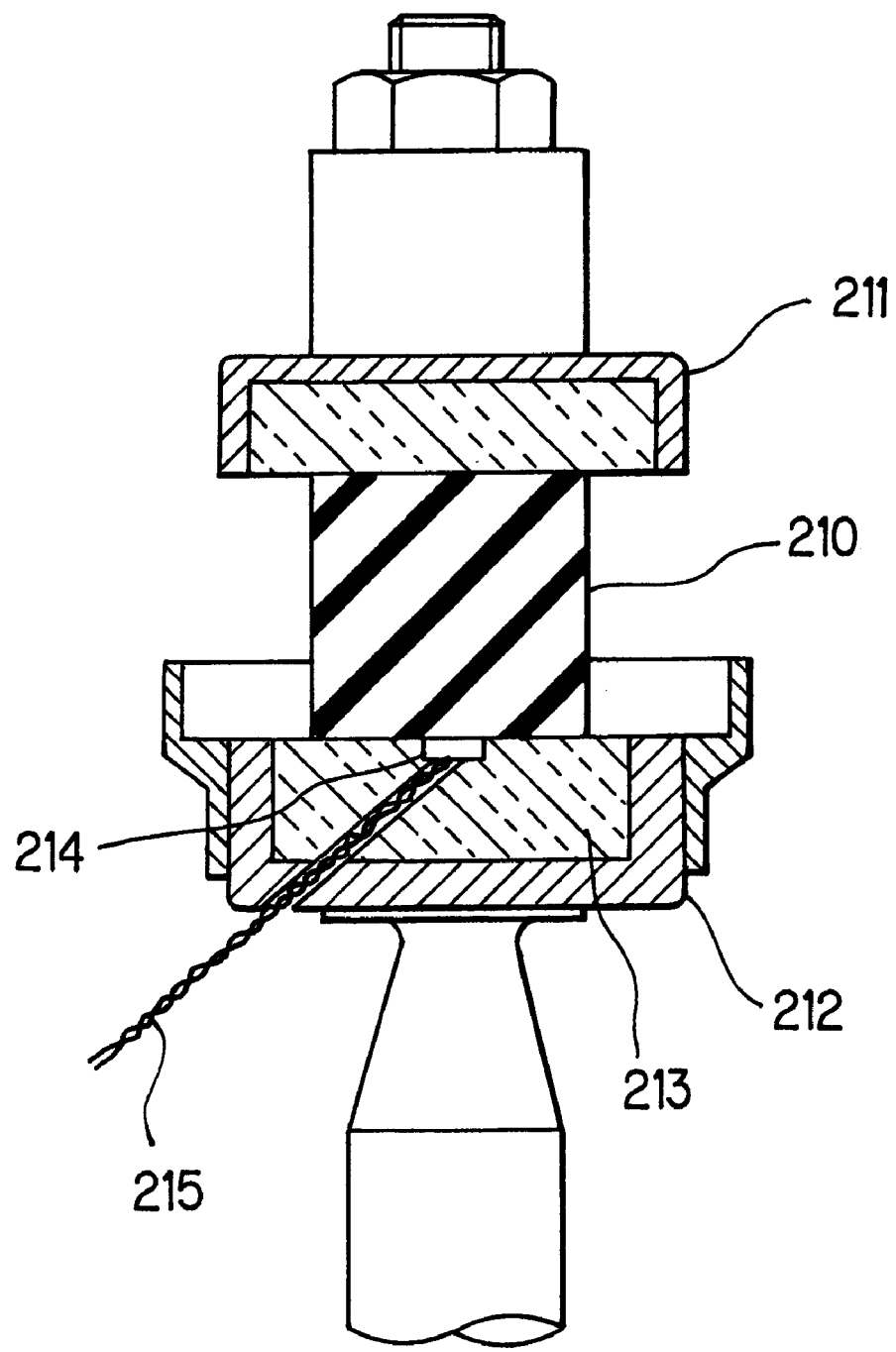
FIG. 16 is a diagram showing the temperature sensor portion of the conventional Goodrich flexometer.
Figure 17:
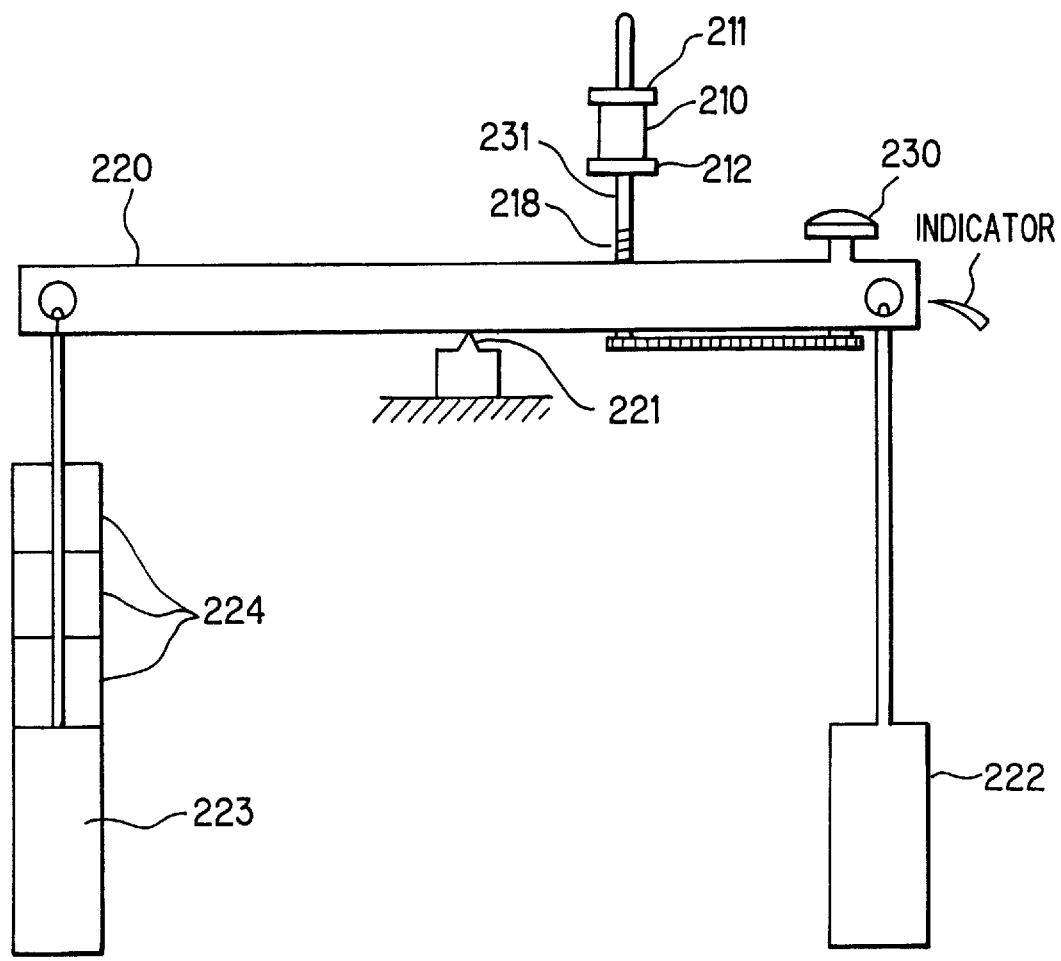
FIG. 17 is a schematic diagram showing the principle of the conventional Goodrich flexometer.

The test piece 51 that has undergone the test is fixed and held by the clamp 82, and is transferred to the sample discharge position 88 by the transfer turret 78. FIG. 14 shows the structure of a sample discharge mechanism.

At the sample discharge position 88, a pusher air cylinder 120 and a sample discharge port are incorporated in the thermostatic chamber 57 on the extension line of the vertical line of the test piece 51. A sample discharge port 121 extends to the outside of the thermostatic chamber 57, and is always closed by a sample discharge port shutter 122, thereby shielding the heat in the thermostatic chamber 57 so that it will not leak to the outside.

When the test piece 51 that has undergone measurement is transferred to the sample discharge position 88 and stops on the sample discharge port 121, a shutter air cylinder 123 is actuated to open the sample discharge port shutter 122. Subsequently, the clamp release air cylinder 84 at the sample discharge position 88 is actuated to open the clamp 82 with the clamp release 83 at the sample discharge position 88. The test piece 51 that has undergone measurement falls through the sample discharge port 121 to be discharged to the outside of the thermostatic chamber 57.

As the test piece 51 naturally falls through the sample discharge port 121, it may sometimes be caught midway along the sample discharge port 121 and cannot be discharged to the outside of the thermostatic chamber 57. For this reason, the pusher air cylinder 120 is actuated to move a pusher 124 at the distal end of the piston downward in the sample discharge port to its lowest portion. Thereafter, the pusher 124 is returned to the highest portion. When this operation ends, the sample discharge port shutter 72 at the sample discharge position 88 is closed by the shutter air cylinder 123. The clamp release 83 is operated to close the clamp 82, and waits for the subsequent movement.

In this manner, transfer, supply, testing, and discharge of the sample are automated, so that the burden on the person in charge of measurement is decreased, thus allowing efficient measurement.

Possibility of Industrial Utilization

As has been described above, in the heat build-up/fatigue measuring method for a viscoelastic body and a hydraulic servo flexometer according to the present invention, since static and dynamic loads are applied by using a hydraulic servo mechanism, highly precise follow-up control and measurement can be performed, and test conditions close to the actual conditions for use can be set. Thus, the present invention is effective in prediction and detection of the heat build-up characteristics, occurrence of blow-out, and the like of viscoelastic bodies.

We claim:

1. A heat build-up/fatigue measuring method which measures heat build-up/fatigue of a viscoelastic body, in which
   a strain and a stress applied to a test piece are detected,
   static and dynamic loads applied to the test piece are controlled by a hydraulic servo mechanism based on the detected strain and stress,
   a creep amount, a complex modulus, and a loss tangent of the test piece are obtained based on the detected strain and stress, and
   a time point at which blow-out will occur is predicted based on changes over time of the creep amount, the complex modulus, the loss tangent, and the temperature of heat build-up of the test piece.

2. A heat build-up/fatigue measuring method which measures heat build-up/fatigue of a viscoelastic body, in which
   a strain and a stress applied to a test piece are detected,
   static and dynamic loads applied to the test piece are controlled by a hydraulic servo mechanism based on the detected strain and stress,
   a loss tangent of the test piece is obtained based on the detected strain and stress, and
   a relationship between a minimum value of loss tangent and a time point at which blow-out occurs is obtained in advance, so that the time point at which blow-out occurs is obtained from the minimum value of the loss tangent.

3. A hydraulic servo flexometer for measuring heat build-up/fatigue of the viscoelastic body, comprising:
   an upper anvil and a lower anvil arranged in a thermostatic chamber to oppose each other to sandwich a viscoelastic test piece;
   a hydraulic servo mechanism for moving said upper anvil or said lower anvil in a vertical direction to apply static and dynamic loads to the test piece;
   hydraulic servo control means for controlling said hydraulic servo mechanism based on a preset test condition;
   a temperature detector for measuring a temperature of the test piece;
   a strain detector for detecting a strain applied to the test piece;
   a stress detector for detecting a stress applied to the test piece;
   a transfer turret which is arranged between said upper anvil and said lower anvil, has an insertion hole formed therein to insert a test piece therein, is provided with fixing means for holding and fixing the test piece inserted in the insertion hole, and rotates intermittently;
   a rotary driving unit for rotating said transfer unit;
   opening means for opening said fixing means, thereby releasing the test piece; and
   a control unit for controlling said hydraulic servo control means, said rotary driving unit, and said opening means to fix the test piece at a supply position with fixing means, rotating said transfer turret until a test position and releasing the test piece, fixing the test piece again with fixing means after the test, and rotating said transfer turret until a discharge position and releasing the test piece.

4. The hydraulic servo flexometer according to claim 3, further comprising:
   a sample supply cylinder arranged above the sample supply position of said transfer turret in a vertical direction and having a sample stopper in a lower side wall to be movable in a transverse direction;
   a vertically movable sample platform arranged vertically below said sample supply cylinder;
   a stopper driving unit for moving said sample stopper in the transverse direction;
   a platform driving unit for moving said sample platform in a vertical direction; and
   a control unit for controlling said stopper driving unit and said platform driving unit to load the sample on said sample platform which has moved upward to a lower end of said sample supply cylinder, and moving said sample platform downward such that the sample is located at a position of said fixing means of said transfer turret.

5. The hydraulic servo flexometer according to claim 3, further comprising:
   a sample discharge port provided vertically below the sample discharge position of said transfer turret;
   a sample discharge port shutter provided at an inlet of said sample discharge port;
   a pusher movable in a vertical direction vertically above the sample discharge port;
   a shutter driving unit for moving said sample discharge port shutter;
   a pusher driving unit for moving said pusher; and
   a control unit for controlling said shutter driving unit and said pusher driving unit to open said shutter and to move said pusher downward only when discharging the test piece.

6. A hydraulic servo flexometer for measuring heat build-up/fatigue of a viscoelastic test piece, comprising:
   an upper anvil and a lower anvil arranged in a thermostatic chamber to oppose each other to sandwich said viscoelastic test piece;
   a hydraulic servo mechanism for moving said upper anvil or said lower anvil in a vertical direction to apply static and dynamic loads to the test piece;
   hydraulic servo control means for controlling said hydraulic servo mechanism based on a preset test condition;
   a temperature detector for measuring a temperature of the test piece;
   a strain detector for detecting a strain applied to the test piece; and
   a stress detector for detecting a stress applied to the tests piece;
   wherein said temperature detector comprises a vertically movable temperature sensor having a pointed distal end, temperature sensor driving means for vertically moving said temperature sensor, and a control unit which performs a control operation in accordance with a detection value of said strain detector so that a distal end of said temperature sensor is located at a center of the test piece.

7. A hydraulic servo flexometer for measuring heat build-up/fatigue of a viscoelastic test piece, comprising:

an upper anvil and a lower anvil arranged in a thermostatic chamber to oppose each other to sandwich a viscoelastic test piece;

a hydraulic servo mechanism for moving said upper anvil or said lower anvil in a vertical direction to apply static and dynamic loads to the test piece;

hydraulic servo control means for controlling said hydraulic servo mechanism based on a preset test condition;

a temperature detector for measuring a temperature of the test piece;

a strain detector for detecting a strain applied to the test piece; and a stress detector for detecting a stress applied to the test piece;

wherein said hydraulic servo flexometer is accommodated and fixed in a hollow frame, and a vibration absorbing member is packed in said frame.

8. A hydraulic servo flexometer for measuring heat build-up/fatigue of a viscoelastic test piece, comprising:

an upper anvil and a lower anvil arranged in a thermostatic chamber to oppose each other to sandwich a viscoelastic test piece;

a hydraulic servo mechanism for moving said upper anvil or said lower anvil in a vertical direction to apply static and dynamic loads to the test piece;

hydraulic servo control means for controlling said hydraulic servo mechanism based on a preset test condition;

a temperature detector for measuring a temperature of the test piece;

a strain detector for detecting a strain applied to the test piece;

a stress detector for detecting a stress applied to the test piece; and an air circulation plate arranged on a surface opposing air blowing means of said thermostatic chamber to circulate air along a side wall.

\* \* \* \* \*